United States Patent
Chen et al.

(10) Patent No.: US 11,845,708 B2
(45) Date of Patent: Dec. 19, 2023

(54) METHOD FOR PHOTOCLEAVAGE OF AMIDE BONDS

(71) Applicant: NANJING TECH UNIVERSITY, Nanjing (CN)

(72) Inventors: Xiaoqiang Chen, Nanjing (CN); Tingwen Wei, Nanjing (CN); Jing Wang, Nanjing (CN); Yanyan Wang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 123 days.

(21) Appl. No.: 17/486,807

(22) Filed: Sep. 27, 2021

(65) Prior Publication Data

US 2022/0289665 A1 Sep. 15, 2022

(30) Foreign Application Priority Data

Mar. 12, 2021 (CN) .......................... 202110267632.4

(51) Int. Cl.
| | | |
|---|---|---|
| *C07C 227/04* | (2006.01) |
| *C07D 209/20* | (2006.01) |
| *C07D 235/22* | (2006.01) |
| *C07D 403/06* | (2006.01) |

(52) U.S. Cl.
CPC .......... *C07C 227/04* (2013.01); *C07D 209/20* (2013.01); *C07D 235/22* (2013.01); *C07D 403/06* (2013.01)

(58) Field of Classification Search
CPC .............................. C07C 227/04; C07D 209/20
See application file for complete search history.

(56) References Cited

U.S. PATENT DOCUMENTS 9,700,881 B2 * 7/2017 Liebeskind ............. C07C 45/46

\* cited by examiner

*Primary Examiner* — Kamal A Saeed
(74) *Attorney, Agent, or Firm* — Perry + Currier Inc.

(57) ABSTRACT

The present disclosure provides a method for photocleavage of an amide bond, the method has mild reaction conditions and can realize the cleavage of amide bonds by using light. The method comprises the following steps: subjecting 2,4-dinitrofluorobenzene to a reaction with an amino group of a substance represented by structural formula I with an α-amino acid at the end to produce a compound 1 represented by structural formula II; then under light irradiation, subjecting the compound 1 to a cleavage reaction of amide bond;

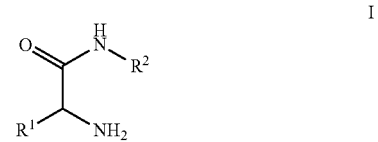

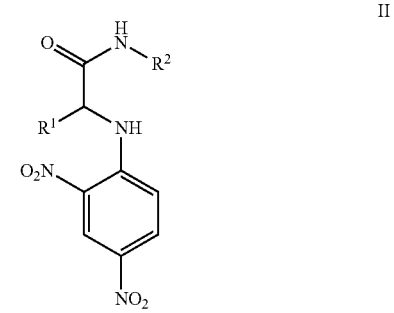

Wherein, R1 is the side chain group of α-amino acid; R2 is: aryl, aliphatic hydrocarbon, —CH(R)—COOH or polypeptide.

7 Claims, 13 Drawing Sheets

METHOD FOR PHOTOCLEAVAGE OF AMIDE BONDS

CROSS REFERENCE TO RELATED APPLICATION

This patent application claims the benefit and priority of Chinese Patent Application No. 202110267632.4 filed on Mar. 12, 2021, the disclosure of which is incorporated by reference herein in its entirety as part of the present application.

TECHNICAL FIELD

The present disclosure relates to a method for cleavage of an amide bond, and more particularly to a method for photocleavage of an amide bond.

BACKGROUND ART

Amide bond (—CO—NH—), in which nitrogen and hydrogen form a single bond, and carbon and oxygen form a double bond. The amide bond is the basic group that constitutes the amide. According to the number of substituents on the nitrogen atom, the amide can be divided into primary amide, secondary amide and tertiary amide. According to the structure, amides can be divided into: amides, lactams, imides and N-substituted amides. In biology, amide bonds, i.e. peptide bonds, are the basic units linking amino acids to form polypeptides and proteins. Since the lone pair of electrons on the nitrogen atom of the amide bond forms a p-π conjugate with the carbonyl group, the C—N bond has partial properties of double bond. The greater the degree of p-π conjugation, the more stable the structure. Therefore, in carboxylic acid derivatives, the amide bond is the most difficult to break, and often requires more severe conditions. At present, the most commonly used method for cleavage of amide bond is heating hydrolysis and enzyme-catalyzed hydrolysis under acid or alkali conditions. The former often needs to be hydrolyzed under strong acid or alkali and high temperature conditions, while the latter is mostly used for the hydrolysis of peptides and proteins. Therefore, the development of methods for cleavage of amide bond with mild reaction conditions has important practical significance.

SUMMARY

The technical problem to be solved by the present disclosure is to overcome the deficiencies of the prior art, and provide a method for photocleavage of an amide bond, the method has mild reaction conditions and can realize the cleavage of the amide bond by using light.

The technical solution of the present disclosure to solve its technical problems is as follows:

A method for photocleavage of an amide bond provided in the present disclosure, wherein comprising the following steps:

Subjecting 2,4-dinitrofluorobenzene to a reaction with an amino group of a substance represented by structural formula I with an α-amino acid at the end to produce a compound 1 represented by structural formula II; then under light irradiation, subjecting the compound 1 to a cleavage reaction of amide bond;

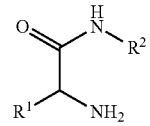

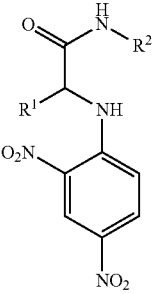

Wherein, $R^1$ is the side chain group of α-amino acid; $R^2$ is: aryl, aliphatic hydrocarbon, —CH(R)—COOH or polypeptide.

The reaction path of the present disclosure is as follows:

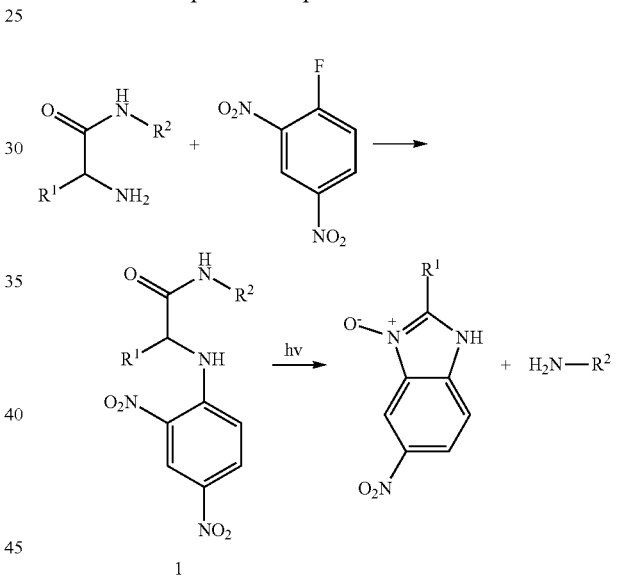

The above method for photocleavage of an amide bond of the present disclosure further includes the following steps: dissolving 2,4-dinitrofluorobenzene in an organic solvent, then dissolving the substance represented by structural formula I with an α-amino acid at the end and NaHCO$_3$ in water, mixing the two in a reaction vessel, and stirring and refluxing at 40-100° C. under darkness for 3-10 h.

The above method for photocleavage of an amide bond of the present disclosure, a further technical solution can also be that the light irradiation wavelength range is 250-550 nm. A further technical solution can also be that the light irradiation time is 0.1 second to 6 h.

The above method for photocleavage of an amide bond of the present disclosure, a further technical solution can also be that the organic solvent is an organic solvent capable of partially or completely dissolving the target lysate, i.e. compound 1. A further technical solution is that the organic solvent is one or a combination of dimethyl sulfoxide, alcohol, ketone, nitrile, ether, and amide. A further technical solution is that the alcohol is methanol, ethanol, butanol, ethylene glycol, n-octanol or isopropanol; the ketone is acetone, methyl ethyl ketone, methyl isobutyl ketone or cyclohexanone; the nitrile is acetonitrile, propionitrile, isobutyronitrile, butyronitrile, malononitrile, benzonitrile, benzyl cyanide, succinonitrile or glutaronitrile; the ether is diethyl ether, tetrahydrofuran, dioxane, glycol dimethyl ether, 2-methyltetrahydrofuran or diphenyl ether; the amide is N,N-dimethylformamide or N,N-dimethylacetamide.

The present disclosure has the following beneficial effects:

1) The present disclosure uses light as energy for cleavage of amide bond, and its source is simple and easy to obtain, low in price, and the environmental pollution is small.

2) The reaction conditions of this reaction are mild, and the amide bond can be cleaved under weak acid or weak base conditions.

3) The amide bond cleavage reaction of the present disclosure is not affected by temperature and has a wide range of applications.

4) The operation of the present disclosure is simple and easy to implement, and it is easy to produce on a large scale.

DETAILED DESCRIPTION OF THE EMBODIMENTS

The present disclosure will be further described in further detail below with reference to the accompanying drawings.

Example 1

[N-(2,4-dinitrophenyl)-L-glycyl]-L-phenylalanine, GLY-PHE

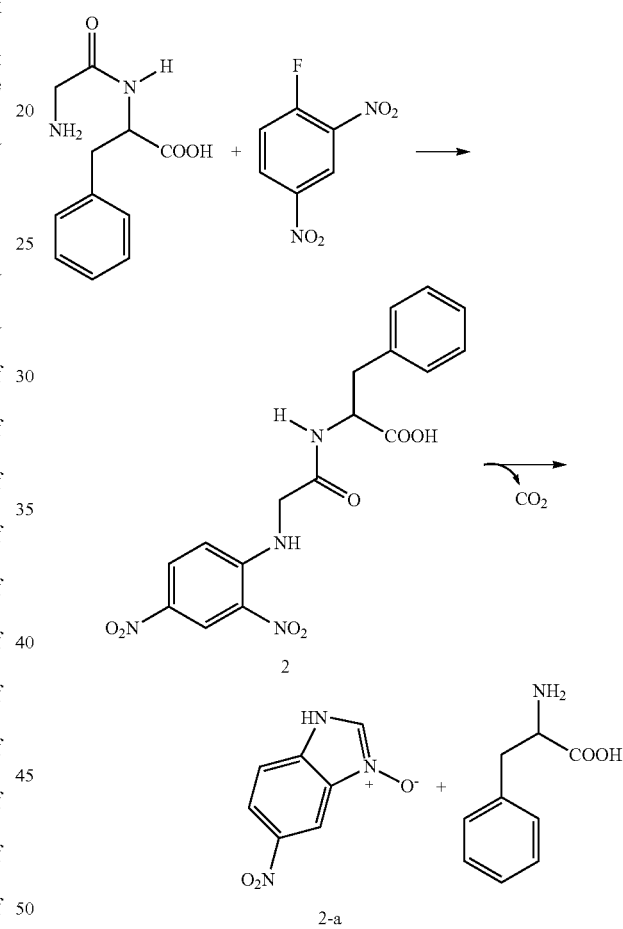

Figure 1:
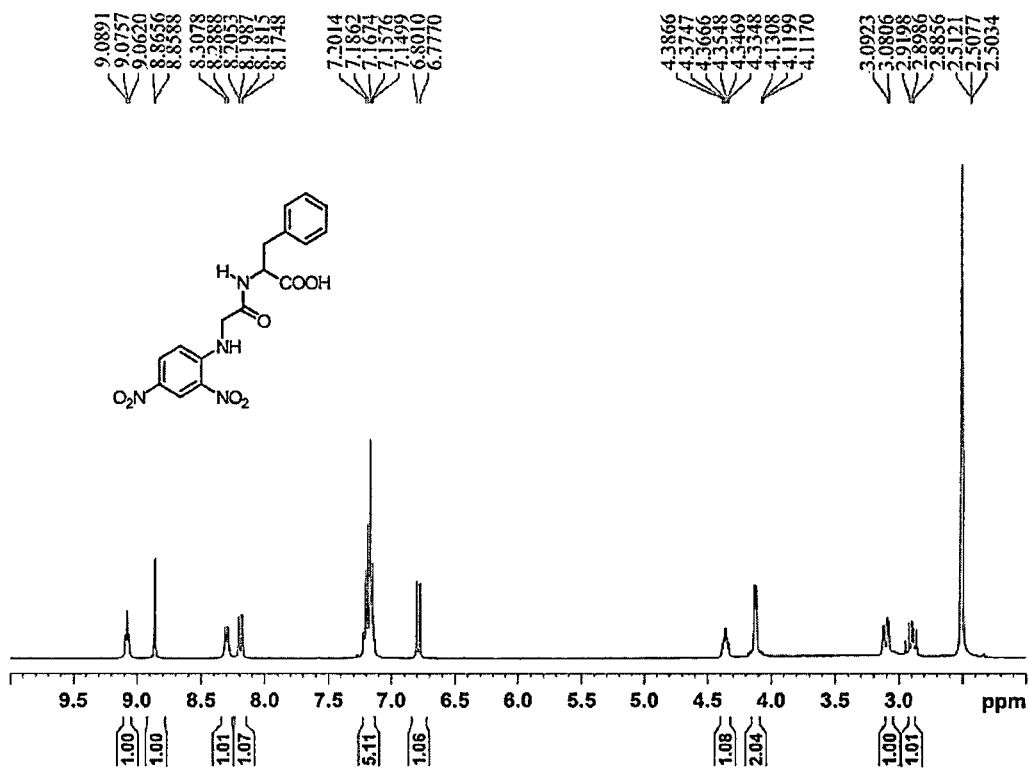
FIG. 1 and FIG. 2 are the $^1$H-NMR spectroscopy and high-resolution mass spectrum of compound 2.
Figure 2:
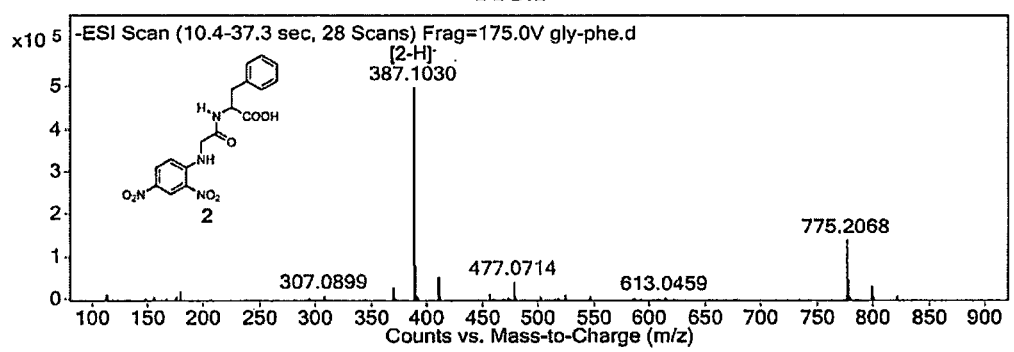
Figure 3:
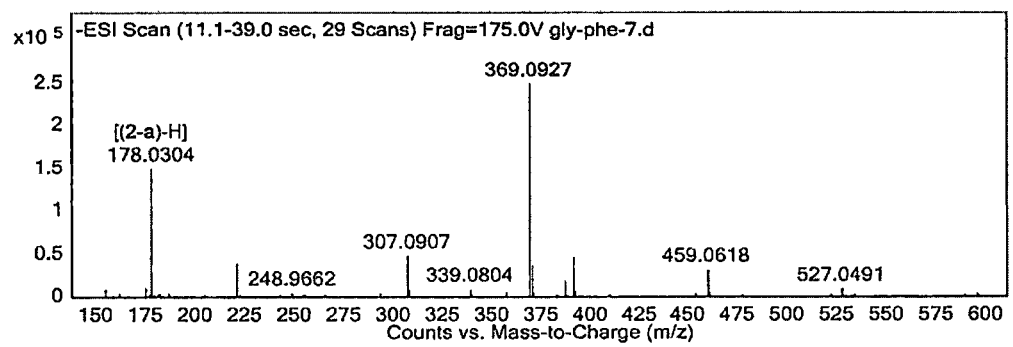
FIG. 3 is the high-resolution mass spectrum of compound 2 after photoreaction.

L-glyto-L-phenylalanine (0.48 g, 2.16 mm) and NaHCO$_3$ (0.3629 g, 4.32 mm) were dissolved in 25 mL deionized water, and (0.45 g, 2.41 mm) 2,4-dinitropylfluorice was dissolved in 10 mL of ethanol solution, and the two were mixed in a 100 mL round bottom flask. The mixture was stirred and refluxed at 80° C. under darkness for 5 h. After spin-drying, 0.75 g of the yellow solid product was separated by a chromatographic column using chloroform and methanol as the eluent, i.e., [N-(2,4-dinitrophenyl)-L-glycyl]-L-phenylalanine ($^1$H-NMR spectroscopy and high-resolution mass spectrum are shown in FIG. 1 and FIG. 2). 0.01 mmol of [N-(2,4-dinitrophenyl)-L-glycinoyl]-L-phenylalanine was dissolved in 10 mL of HPLC methanol solution. The 1 mmol/L standard solution was prepared, 10 μL of the standard solution was added to 290 μL of deionized aqueous solution (pH=7), and mass spectrum data was recorded after 365 nm ultraviolet light. From the mass spectrum data, the characteristic mass spectrum peak of 5-nitro-1H-benzo[d]imidazole-3-oxide (2-a) can be clearly observed (see FIG. 3).

Example 2

[N-(2,4-dinitrophenyl)-L-alanyl]-L-alanine, ala-ala

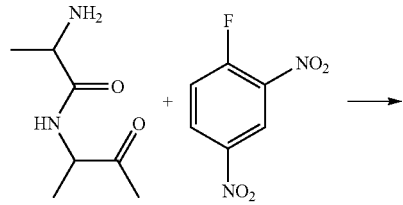

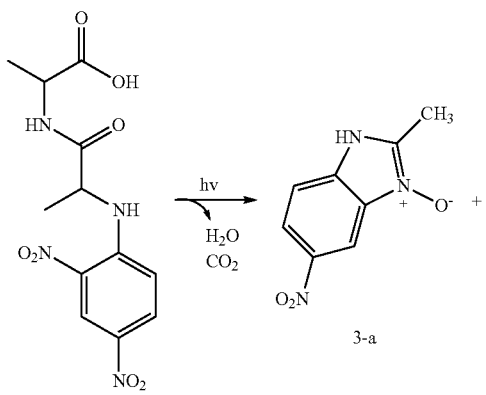

Figure 4:
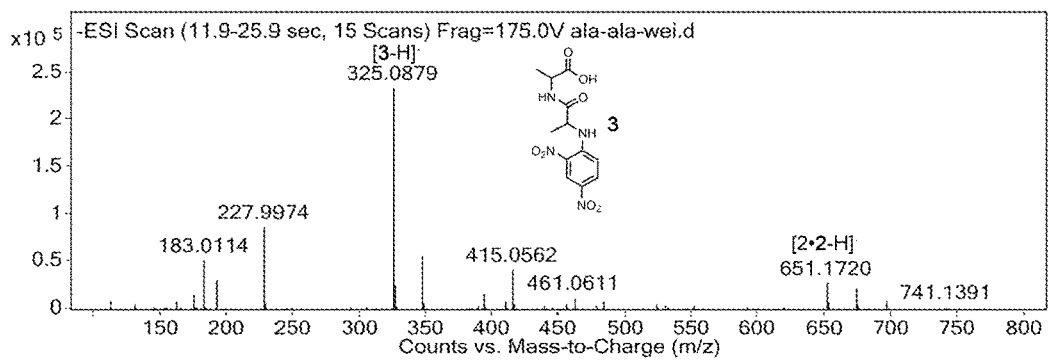
FIG. 4 and FIG. 5 are high-resolution mass spectra of compound 3 and after photoreaction.
Figure 5:
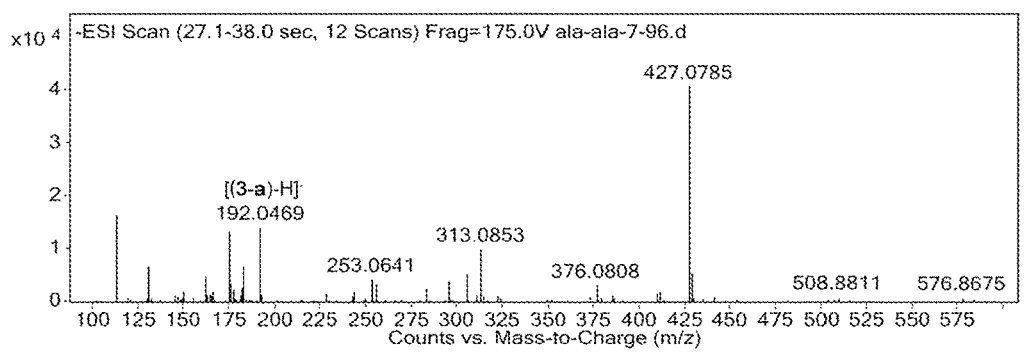

(0.15 mM) L-alanyl-L-alanine and (0.3 mm) NaHCO$_3$ were dissolved in 3.5 mL of deionized water, (0.18 mM) 2,4-dinitrofluorobenzene was dissolved in 2.5 mL of ethanol solution, and the two were mixed in a 25 mL flask, and the mixture was stirred at 50° C. under darkness for 4 h to obtain a yellow mixture. 5 μL of the mixture was added to 10 mL of the deionized aqueous solution (pH=7) to give the solution to be photolyzed. The characteristic peak of [N-(2,4-dinitrophenyl)-L-alanyl]-L-alanine (compound 3) can be clearly observed from the mass spectrum of the solution to be photolyzed (see FIG. 4)). 200 μL of the solution to be photolyzed was placed in a glass 96-well plate, irradiated with 365 nm ultraviolet light for 10 min, the mass spectrum data was recorded, and the characteristic mass spectrum peak of 2-methyl-5-nitro-1H-benzo[d]imidazole-3-oxide (3-a) can be clearly observed (see FIG. 5).

Example 3

[N-(2,4-dinitrophenyl)-L-alanyl]-L-glycine, ala-gly

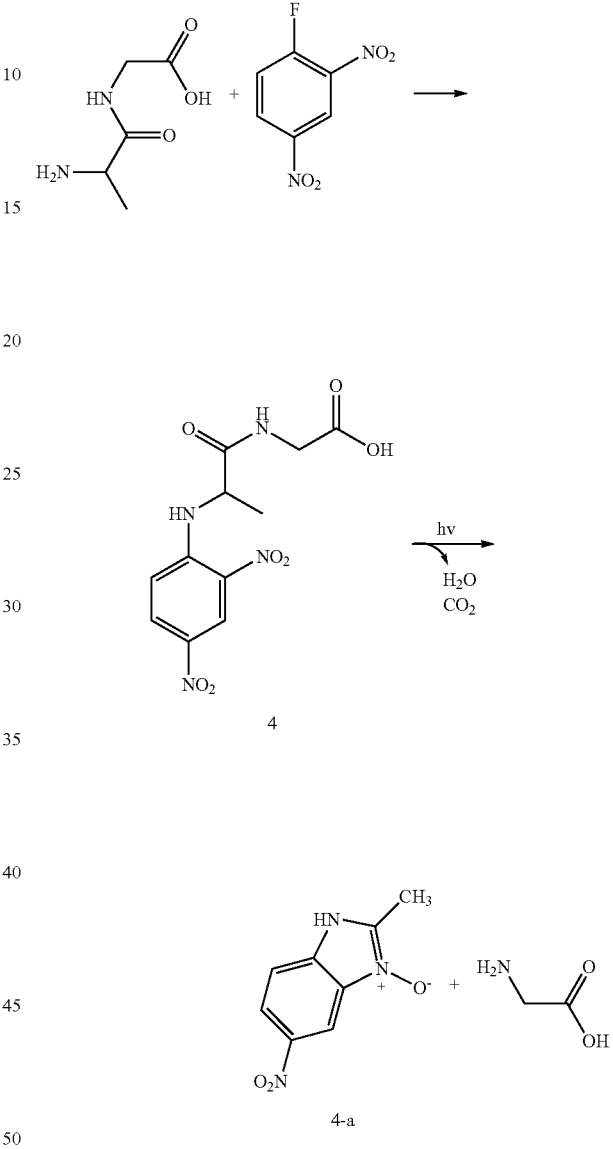

Figure 6:
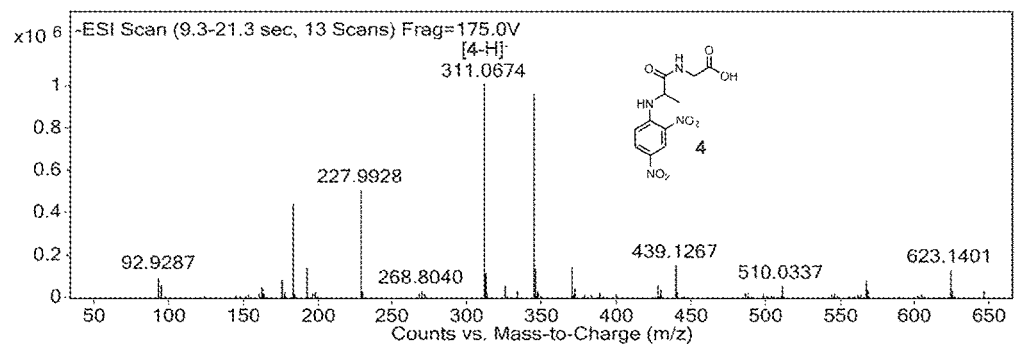
FIG. 6 and FIG. 7 are high-resolution mass spectra of compound 4 and after photoreaction.
Figure 7:
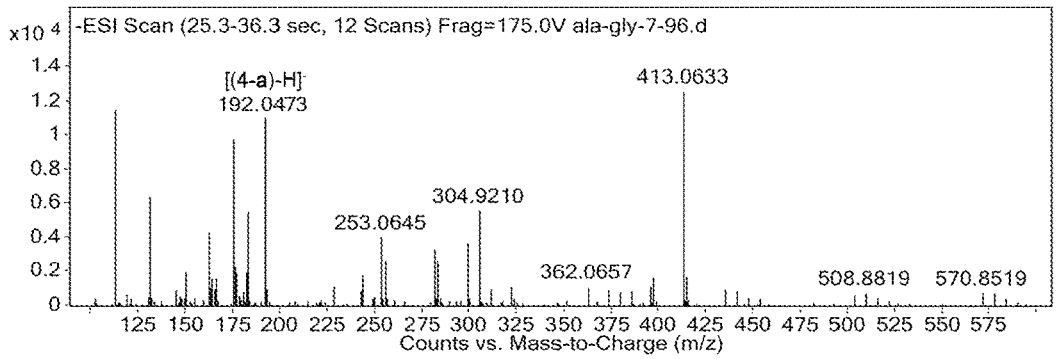

In the same conditions as in Example 2, L-alanyl-L-glycine was reacted with 2,4-dinitrofluorobenzene, and the characteristic peak of [N-(2,4-dinitrophenyl)-L-alanyl]-L-glycine (compound 3) can be clearly observed on the mass spectrum data after the reaction (see FIG. 6). Under the same conditions as in Example 2, the compound 3 was subjected to a photocleavage reaction, the characteristic peak of 2-methyl-5-nitro-1H-benzo[d]imidazole-3-oxide (3-a) can be clearly observed on the mass spectrum after the photoreaction (see FIG. 7).

Example 4

[N-(2,4-dinitrophenyl)-L-histidyl]-L-leucine His-leu

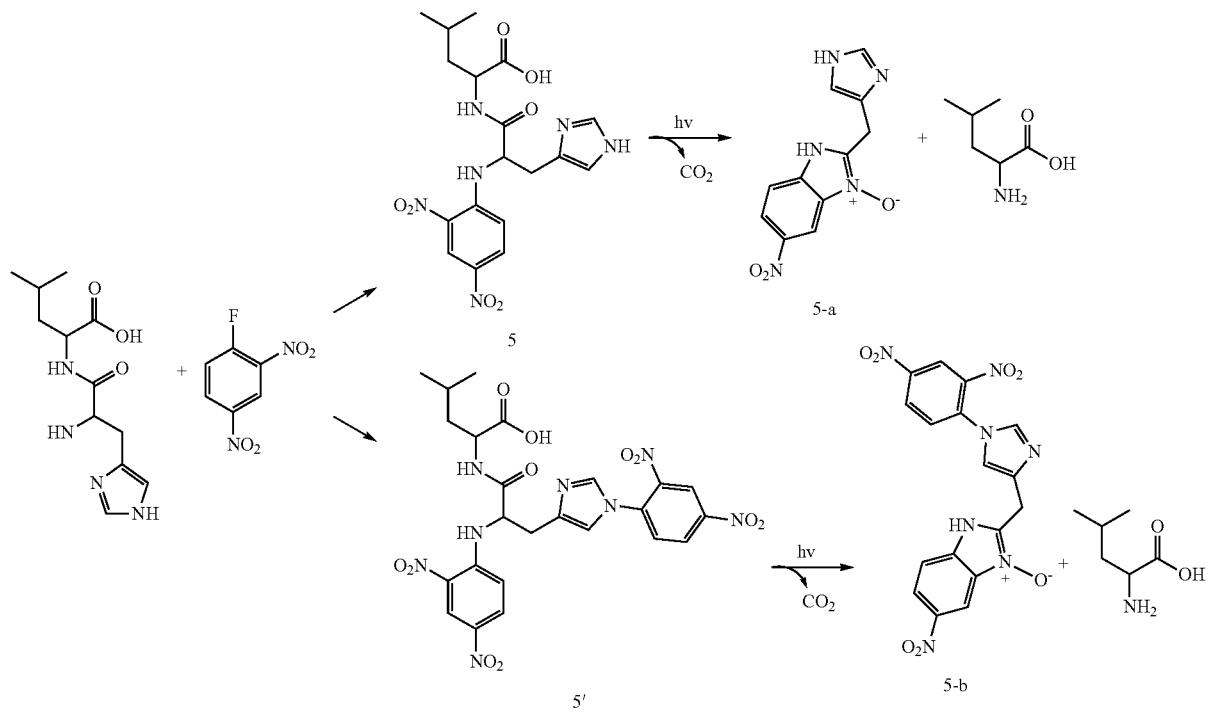

Figure 8:
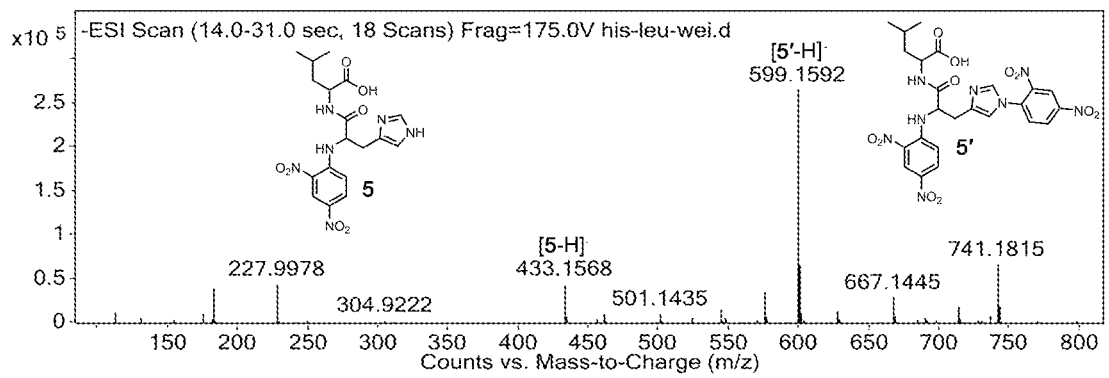
FIG. 8 and FIG. 9 are high-resolution mass spectra of compound 5 and after photoreaction.
Figure 9:
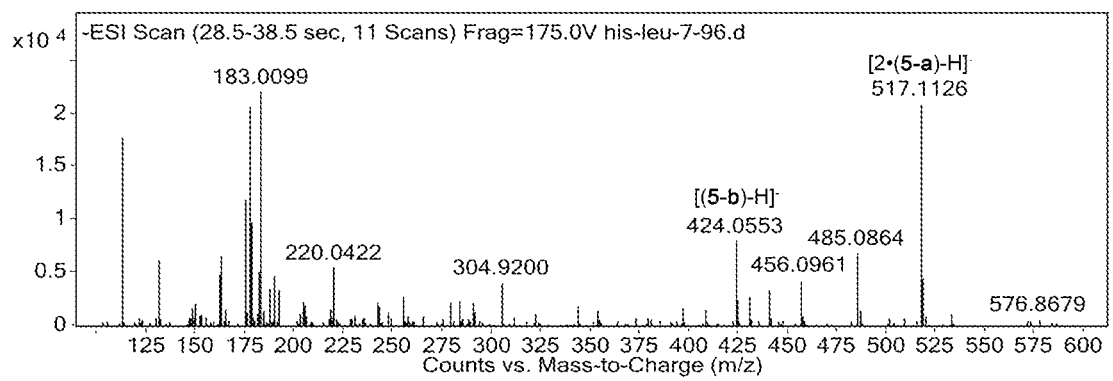

Under the same conditions as in Example 2, L-histidyl-L-leucine was reacted with 2,4-dinitrofluorobenzene, and the characteristic peaks of [N-(2, 4-dinitrophenyl)-L-histaminoyl]-L-leucine (compound 5) and [N,N'-bis(2, 4-dinitrophenyl) L-histaminoyl]-L-leucine (compound 5') could be clearly observed on the mass spectrum data after the reaction (See FIG. 8). Under the same conditions as in Example 2, compound 5 and compound 5' were subjected to photocleavage reaction, and the characteristic peaks of 2-[1H-imidazol-4-yl)methyl]-5-nitro-1H-benzo[d]imidazole-3-oxide (5-a) and 2-[1-(2,4-dinitrophenyl)-1H-imidazol-4-yl)methyl)-5-nitro-1H-benzo[d]imidazole-3-oxide (5-b) could be clearly observed on the mass spectrum data after the reaction (see FIG. 9).

Example 5

[N-(2,4-dinitrophenyl)-L-alanyl]-L-phenylalanine Ala-phe

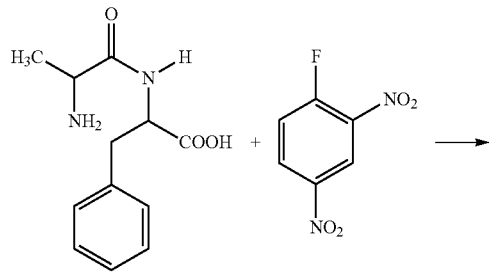

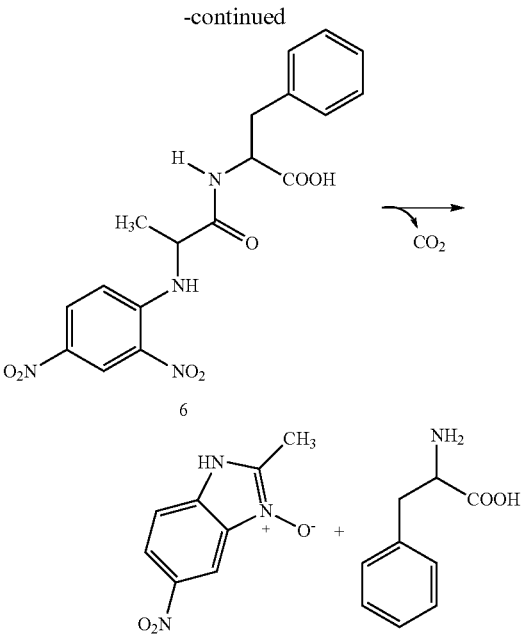

Figure 10:
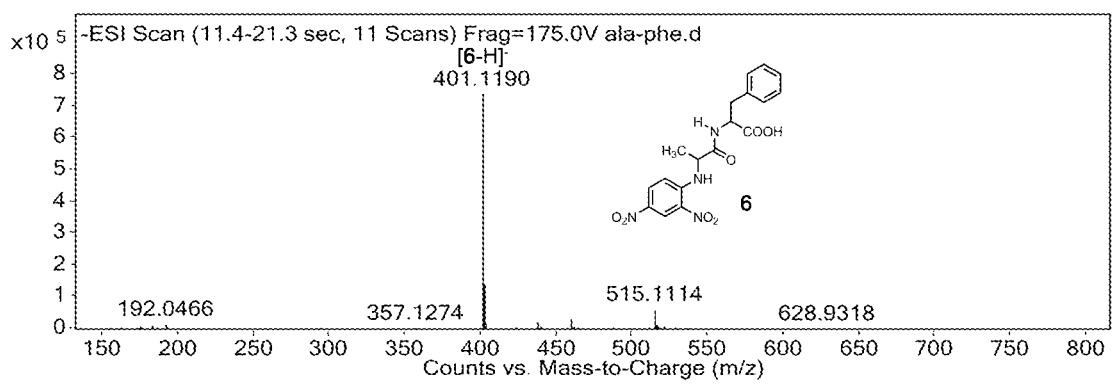
FIG. 10 and FIG. 11 are high-resolution mass spectra of compound 6 and after photoreaction.

Under the same conditions as in Example 2, L-alanyl-L-phenylalanine was reacted with 2,4-dinitrofluorobenzene, the characteristic peak of [N-(2,4-dinitrophenyl)-L-alanyl]-L-phenylalanine (compound 6) can be clearly observed on the mass spectrum data after the reaction (see FIG. 10).

Figure 11:
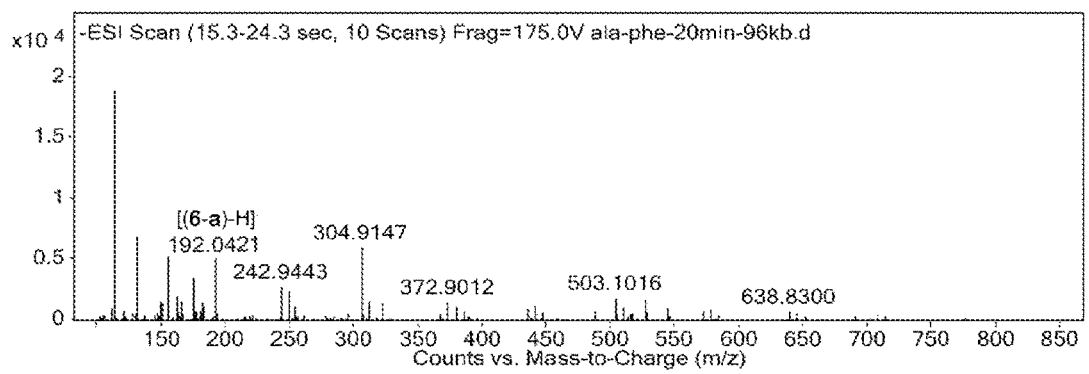

Under the same conditions as in Example 2, compound 6 was subjected to a photocleavage reaction, the characteristic peak of 2-methyl-5-nitro-1H-benzo[d]imidazole-3-oxide (6-a) can be clearly observed on the mass spectrum after the photoreaction (see FIG. 11).

Example 6

[N-(2,4-dinitrophenyl)-L-alanyl]-L-glutamine Ala-gln

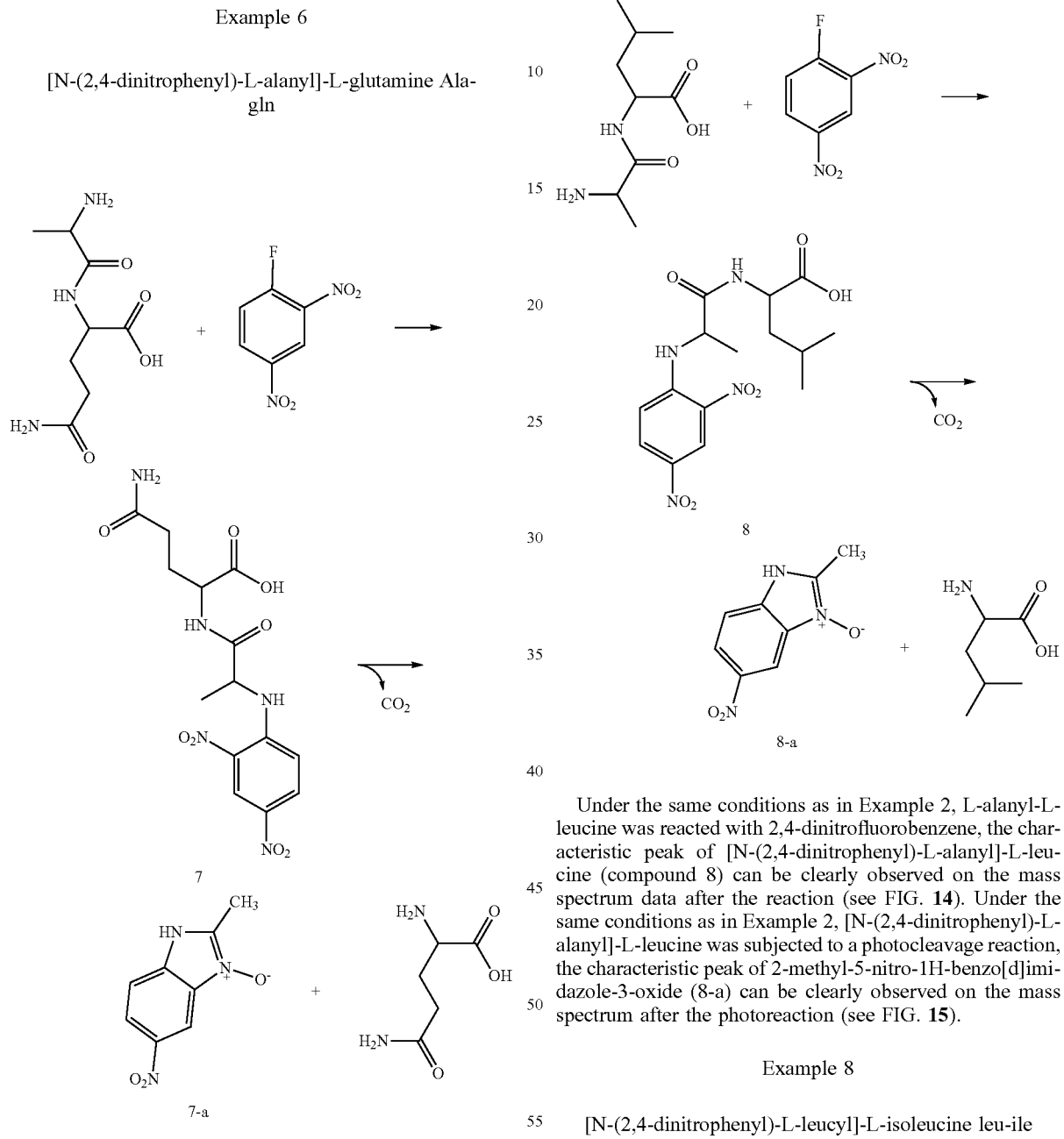

Figure 12:
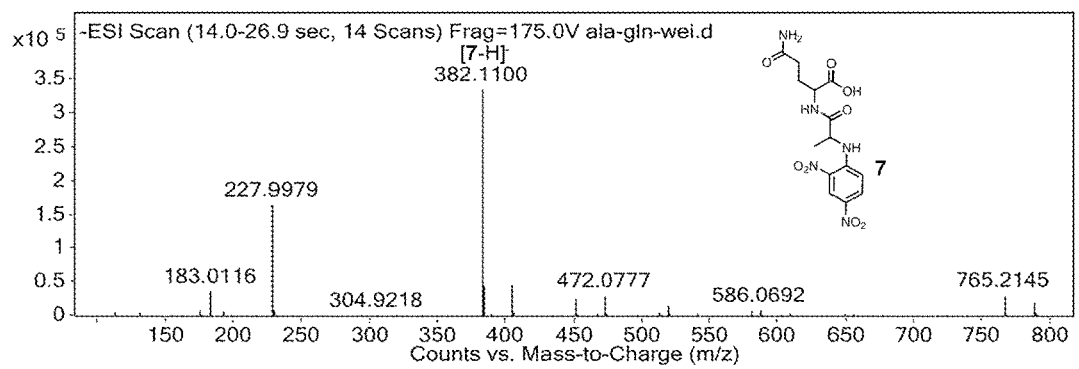
FIG. 12 and FIG. 13 are high-resolution mass spectra of compound 7 and after photoreaction.
Figure 13:
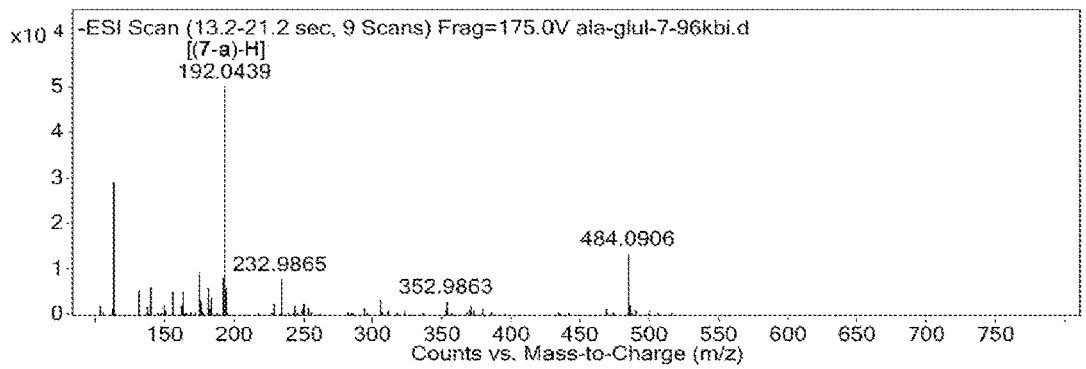

Under the same conditions as in Example 2, L-alanyl-L-glutamine was reacted with 2,4-dinitrofluorobenzene, the characteristic peak of [N-(2,4-dinitrophenyl)-L-alanyl]-L-glutamine (compound 7) can be clearly observed on the mass spectrum data after the reaction (see FIG. 12). Under the same conditions as in Example 2, [N-(2,4-dinitrophenyl)-L-alanyl]-L-glutamine was subjected to a photocleavage reaction, the characteristic peak of 2-methyl-5-nitro-1H-benzo[d]imidazole-3-oxide (7-a) can be clearly observed on the mass spectrum after the photoreaction (see FIG. 13).

Example 7

[N-(2,4-dinitrophenyl)-L-alanyl]-L-leucine Ala-leu

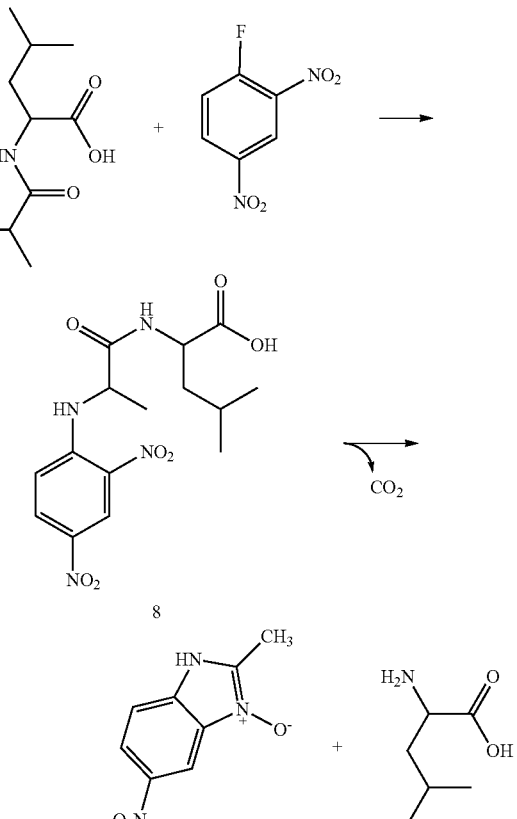

Figure 14:
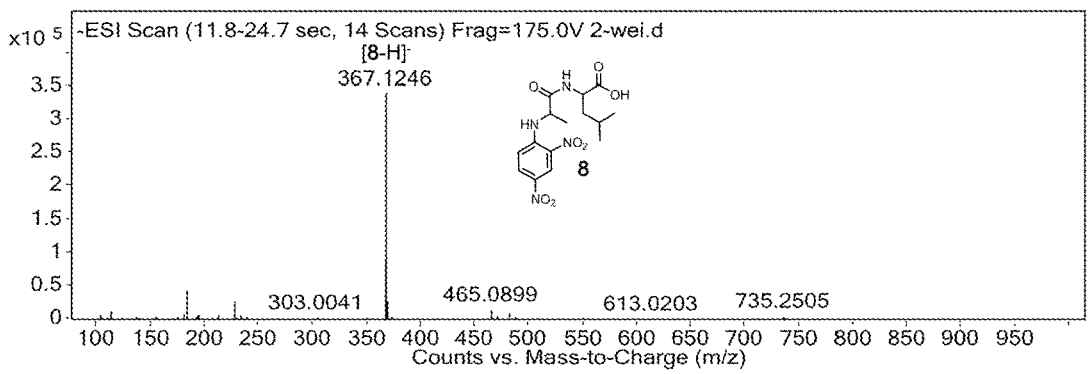
FIG. 14 and FIG. 15 are high-resolution mass spectra of compound 8 and after photoreaction.
Figure 15:
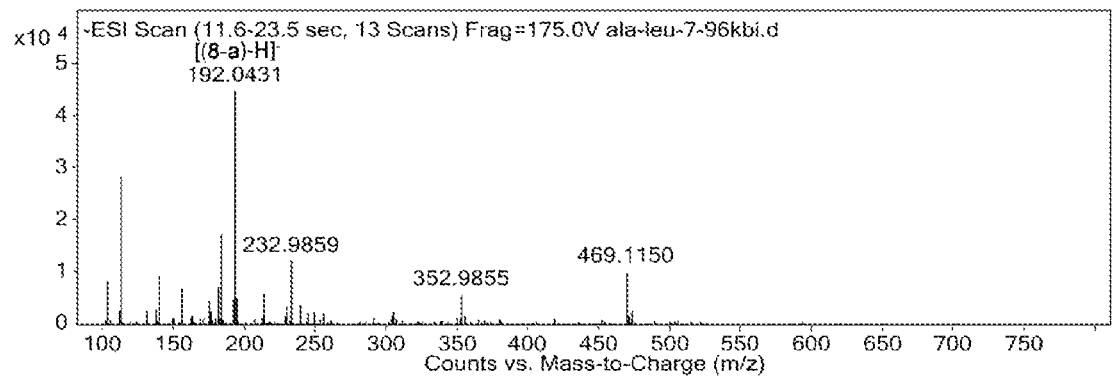

Under the same conditions as in Example 2, L-alanyl-L-leucine was reacted with 2,4-dinitrofluorobenzene, the characteristic peak of [N-(2,4-dinitrophenyl)-L-alanyl]-L-leucine (compound 8) can be clearly observed on the mass spectrum data after the reaction (see FIG. 14). Under the same conditions as in Example 2, [N-(2,4-dinitrophenyl)-L-alanyl]-L-leucine was subjected to a photocleavage reaction, the characteristic peak of 2-methyl-5-nitro-1H-benzo[d]imidazole-3-oxide (8-a) can be clearly observed on the mass spectrum after the photoreaction (see FIG. 15).

Example 8

[N-(2,4-dinitrophenyl)-L-leucyl]-L-isoleucine leu-ile

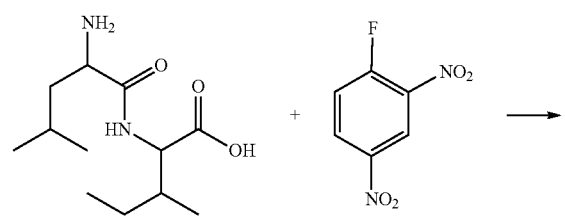

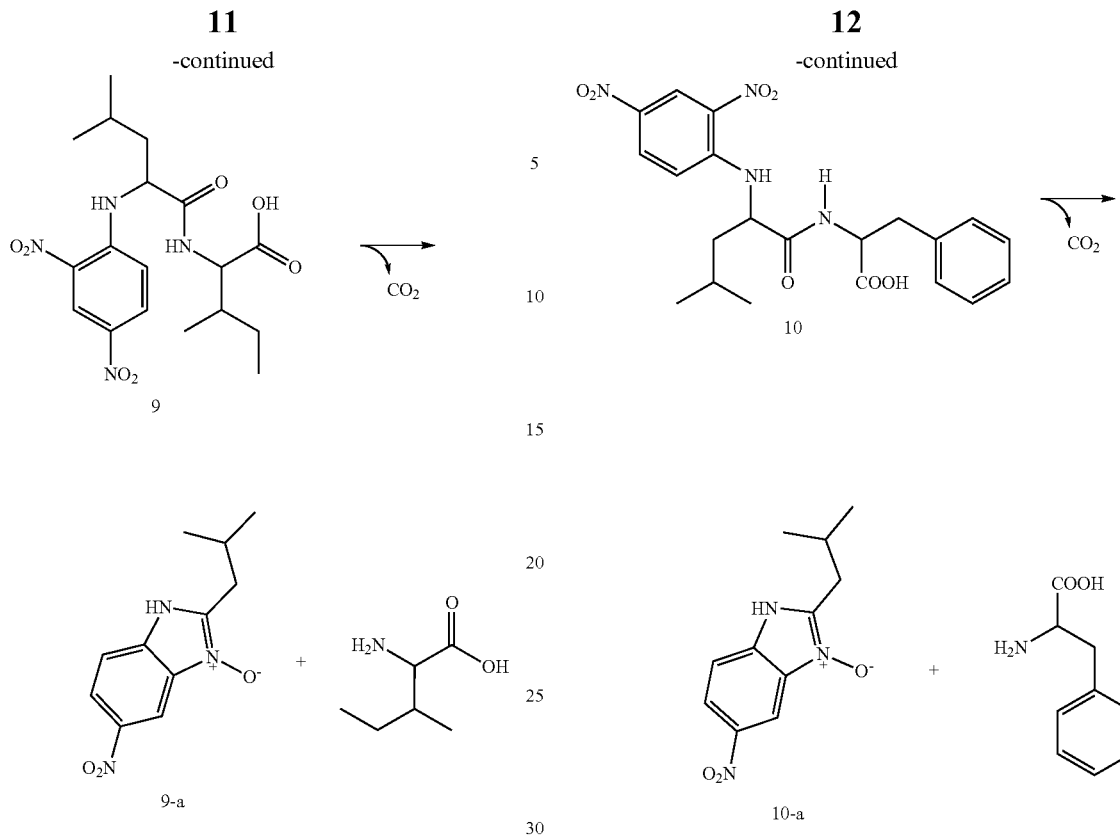

9

9-a

10

10-a

Figure 16:
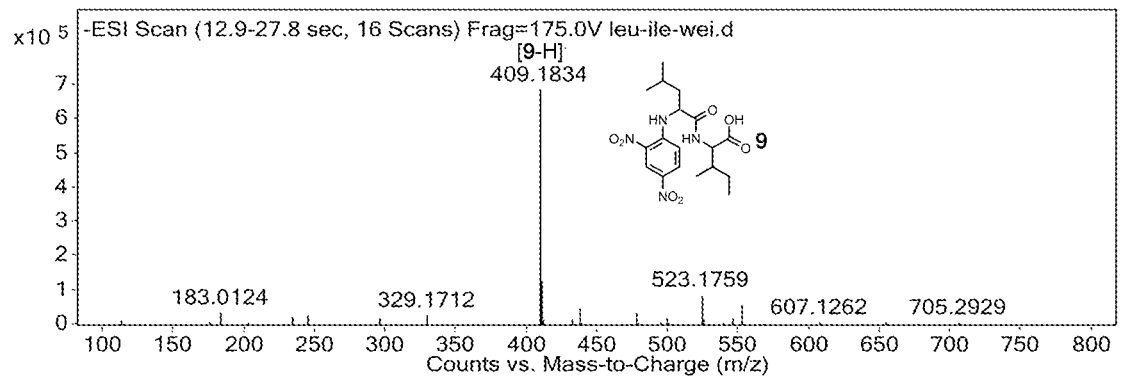
FIG. 16 and FIG. 17 are high-resolution mass spectra of compound 9 and after photoreaction.
Figure 17:
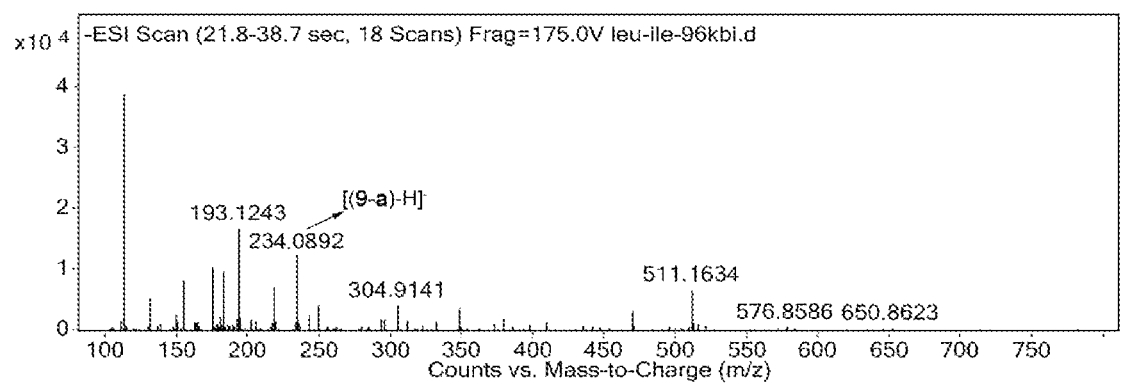

Under the same conditions as in Example 2, L-leucyl-L-isoleucine was reacted with 2,4-dinitrofluorobenzene, the characteristic peak of [N-(2,4-dinitrophenyl)-L-leucyl]-L-isoleucine (compound 9) can be clearly observed on the mass spectrum data after the reaction (see FIG. 16). Under the same conditions as in Example 2, [N-(2,4-dinitrophenyl)-L-leucyl]-L-isoleucine was subjected to a photocleavage reaction, the characteristic peak of 2-isobutyl-5-nitro-1H-benzo[d]imidazole-3-oxide (9-a) can be clearly observed on the mass spectrum after the photoreaction (see FIG. 17).

Example 9

[N-(2,4-dinitrophenyl)-L-leucyl]-L-phenylalanine leu-phe

Figure 18:
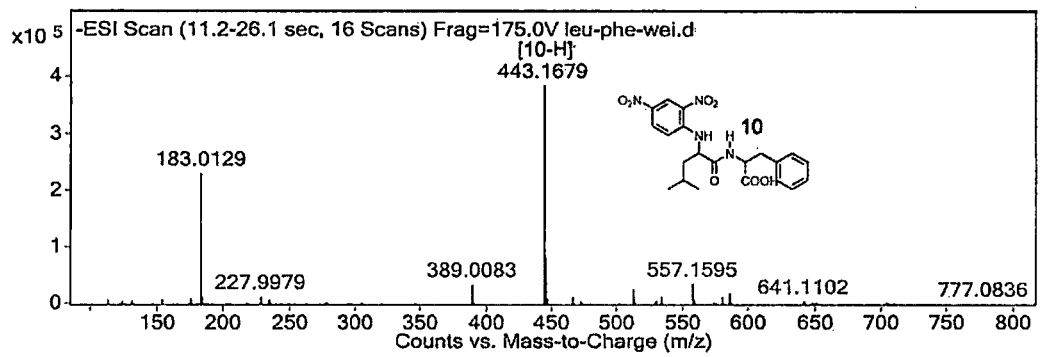
FIG. 18 and FIG. 19 are high-resolution mass spectra of compound 10 and after photoreaction.
Figure 19:
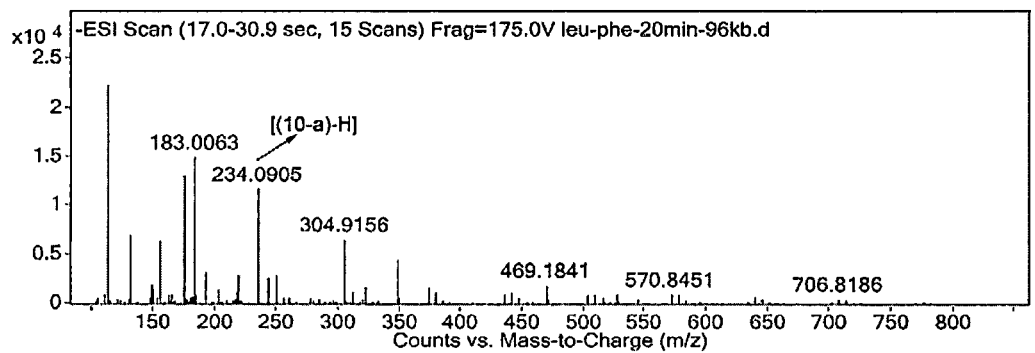

Under the same conditions as in Example 2, L-leucyl-L-phenylalanine was reacted with 2,4-dinitrofluorobenzene, the characteristic peak of [N-(2,4-dinitrophenyl)-L-leucyl]-L-phenylalanine (compound 10) can be clearly observed on the mass spectrum data after the reaction (see FIG. 18). Under the same conditions as in Example 2, [N-(2,4-dinitrophenyl)-L-leucyl]-L-phenylalanine was subjected to a photocleavage reaction, the characteristic peak of 2-isobutyl-5-nitro-1H-benzo[d]imidazole-3-oxide (10-a) can be clearly observed on the mass spectrum after the photoreaction (see FIG. 19).

Example 10

[N-(2,4-dinitrophenyl)-L-leucyl]-L-leucine leu-leu

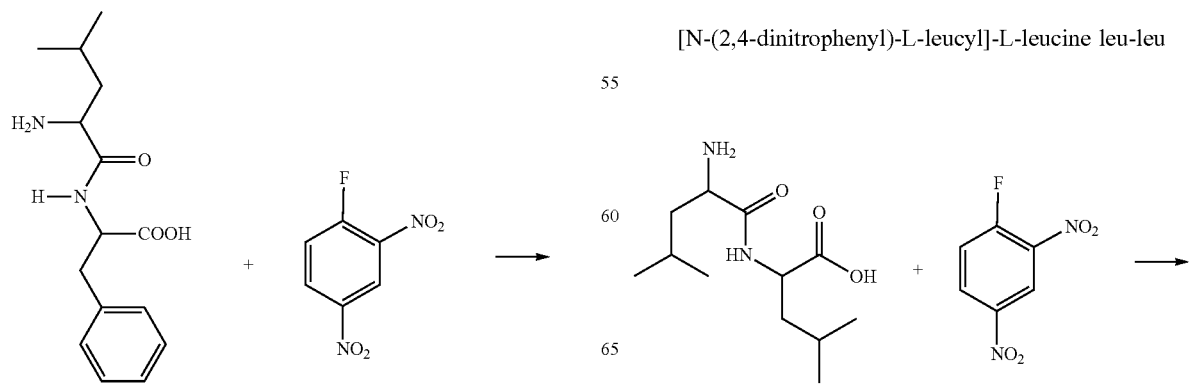

13

-continued

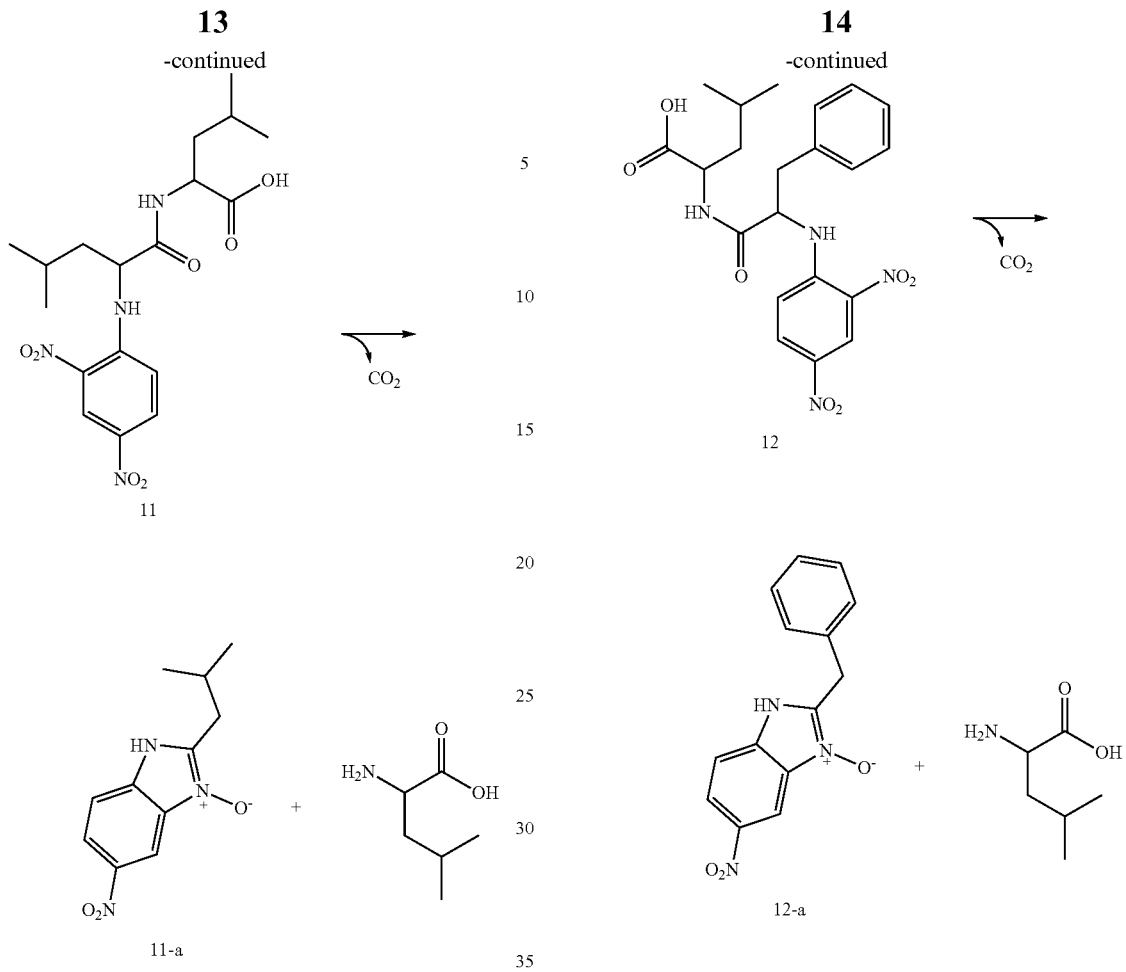

Figure 20:
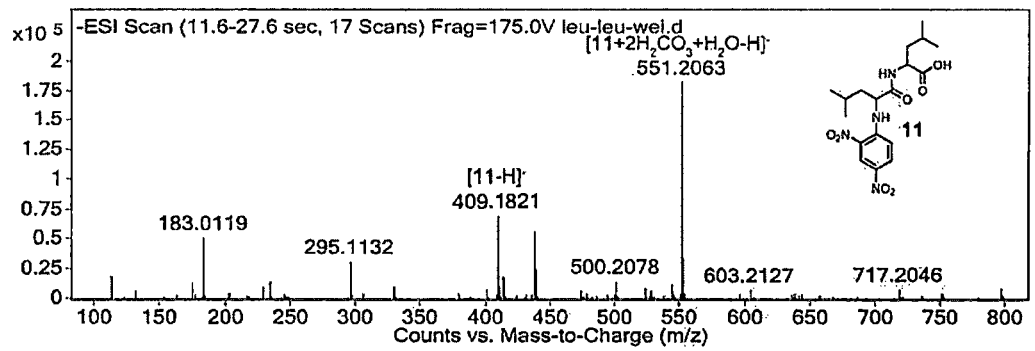
FIG. 20 and FIG. 21 are high-resolution mass spectra of compound 11 and after photoreaction.
Figure 21:
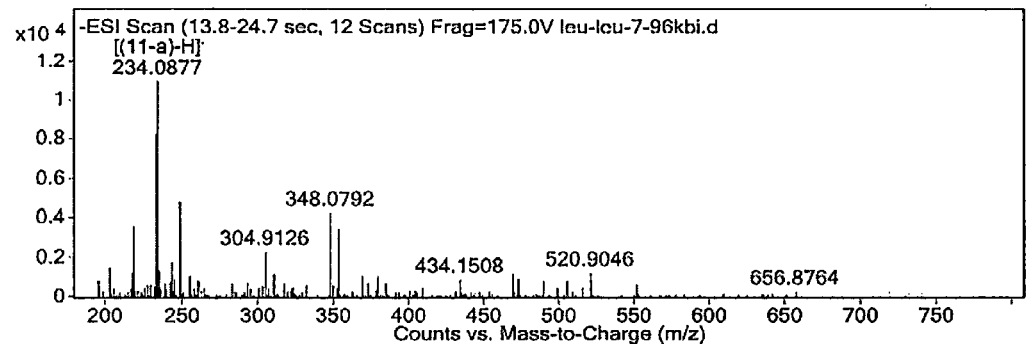

Under the same conditions as in Example 2, L-leucyl-L-leucine was reacted with 2,4-dinitrofluorobenzene, the characteristic peak of [N-(2,4-dinitrophenyl)-L-leucyl]-L-leucine (compound 11) can be clearly observed on the mass spectrum data after the reaction (see FIG. 20). Under the same conditions as in Example 2, [N-(2,4-dinitrophenyl)-L-leucyl]-L-leucine was subjected to a photocleavage reaction, the characteristic peak of 2-isobutyl-5-nitro-1H-benzo[d]imidazole-3-oxide (11-a) can be clearly observed on the mass spectrum after the photoreaction (see FIG. 21).

Figure 22:
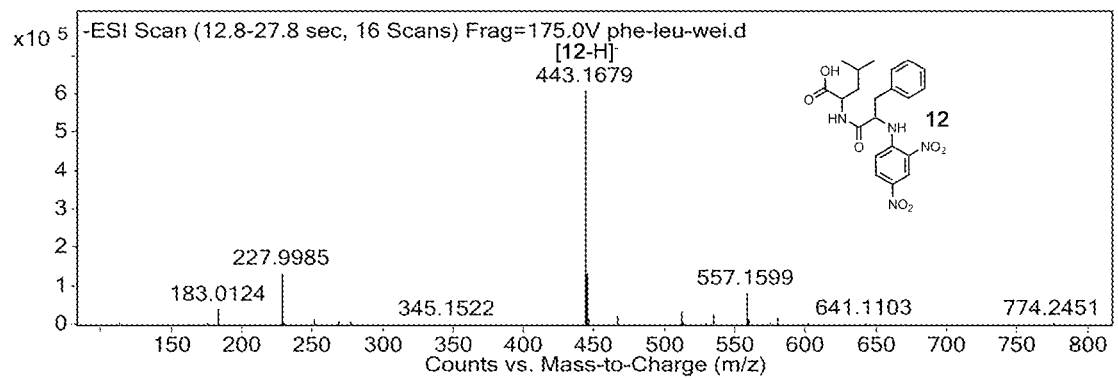
FIG. 22 and FIG. 23 are high-resolution mass spectra of compound 12 and after photoreaction.
Figure 23:
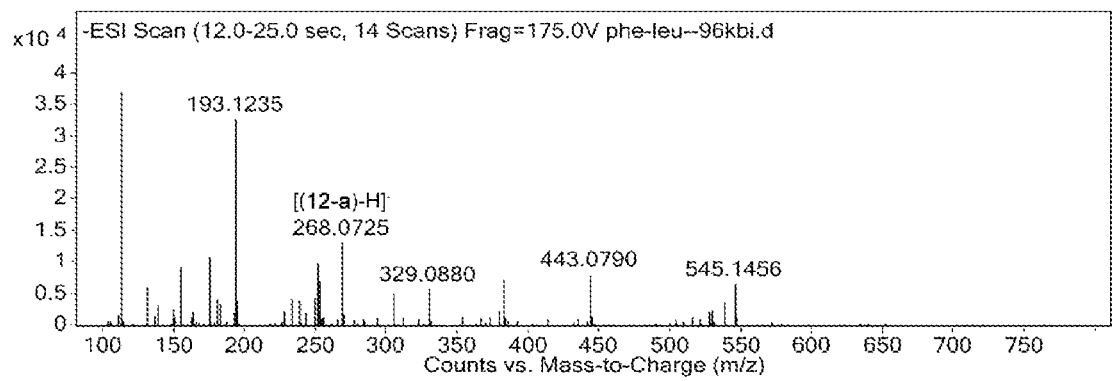

Under the same conditions as in Example 2, L-phenylalanyl-L-leucine was reacted with 2,4-dinitrofluorobenzene, the characteristic peak of [N-(2,4-dinitrophenyl)-L-phenylalanyl]-L-leucine (compound 12) can be clearly observed on the mass spectrum data after the reaction (see FIG. 22). Under the same conditions as in Example 2, [N-(2,4-dinitrophenyl)-L-phenylalanyl]-L-leucine was subjected to a photocleavage reaction, the characteristic peak of 2-benzyl-5-nitro-1H-benzo[d]imidazole-3-oxide (12-a) can be clearly observed on the mass spectrum after the photoreaction (see FIG. 23).

Example 11

[N-(2,4-dinitrophenyl)-L-phenylalanyl]-L-leucine
phe-leu

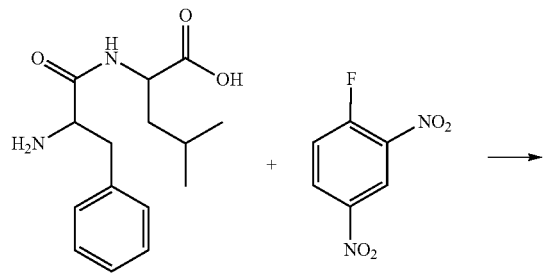

Example 12

[N-(2,4-dinitrophenyl)-L-phenylalanyl]-L-alanine
phe-ala

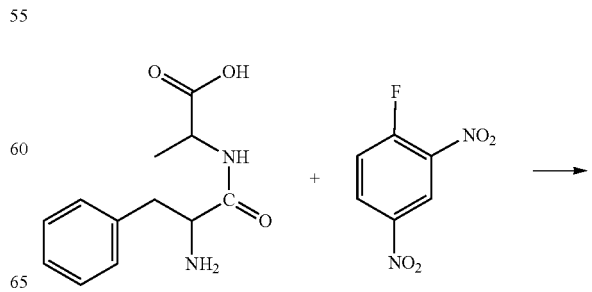

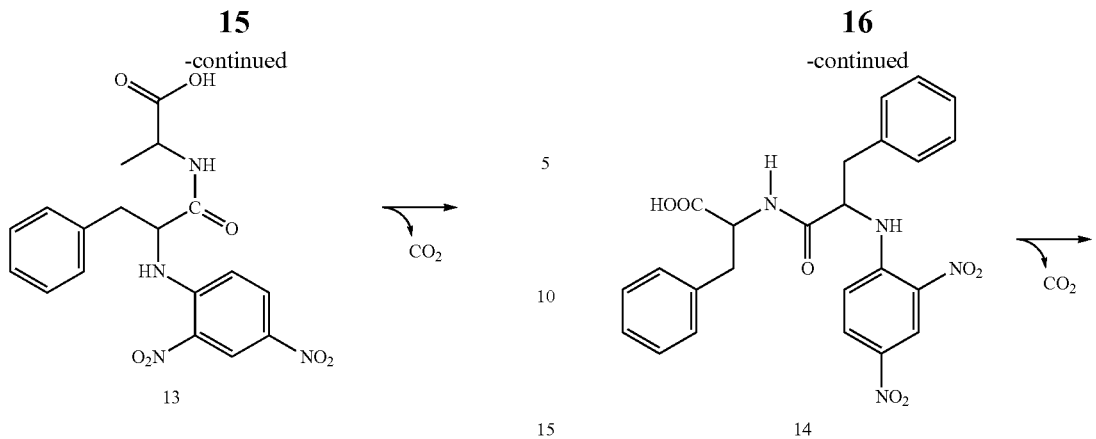

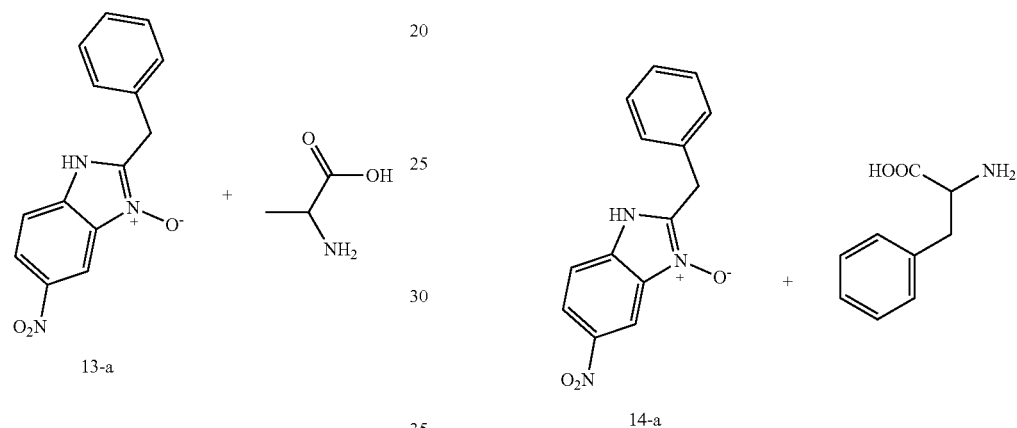

Figure 24:
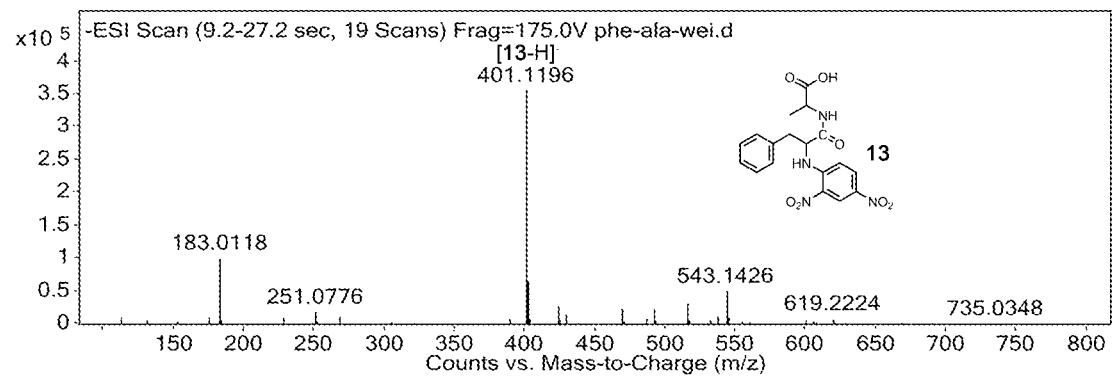
FIG. 24 and FIG. 25 are high-resolution mass spectra of compound 13 and after photoreaction.
Figure 25:
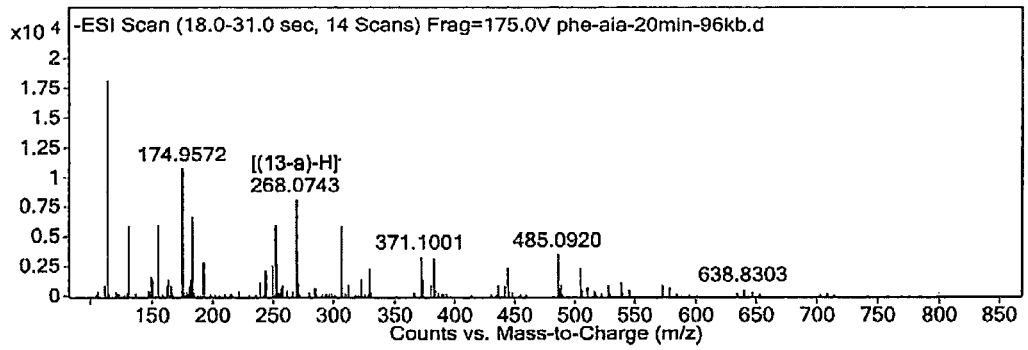

Under the same conditions as in Example 2, L-phenylalanyl-L-alanine was reacted with 2,4-dinitrofluorobenzene, the characteristic peak of [N-(2,4-dinitrophenyl)-L-phenylalanyl]-L-alanine (compound 13) can be clearly observed on the mass spectrum data after the reaction (see FIG. 24). Under the same conditions as in Example 2, [N-(2,4-dinitrophenyl)-L-phenylalanyl]-L-alanine was subjected to a photocleavage reaction, the characteristic peak of 2-benzyl-5-nitro-1H-benzo[d]imidazole-3-oxide (13-a) can be clearly observed on the mass spectrum after the photoreaction (see FIG. 25).

Example 13

[N-(2,4-dinitrophenyl)-L-phenylalanyl]-L-phenylalanine phe-phe

Figure 26:
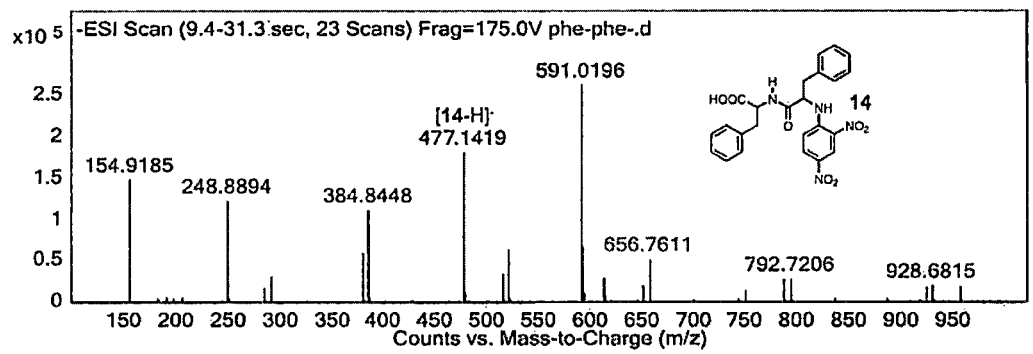
FIG. 26 and FIG. 27 are high-resolution mass spectra of compound 14 and after photoreaction.
Figure 27:
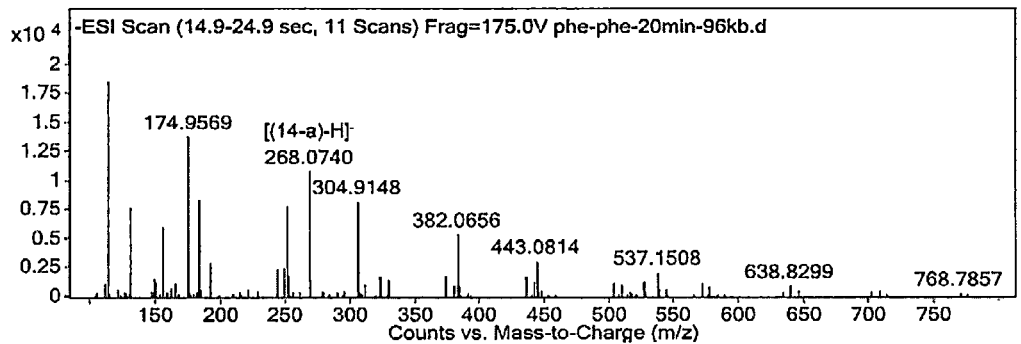

Under the same conditions as in Example 2, L-phenylalanyl-L-phenylalanine was reacted with 2,4-dinitrofluorobenzene, the characteristic peak of [N-(2,4-dinitrophenyl)-L-phenylalanyl]-L-phenylalanine (compound 13) can be clearly observed on the mass spectrum data after the reaction (see FIG. 26). Under the same conditions as in Example 2, [N-(2,4-dinitrophenyl)-L-phenylalanyl]-L-phenylalanine was subjected to a photocleavage reaction, the characteristic peak of 2-benzyl-5-nitro-1H-benzo[d]imidazole-3-oxide (13-a) can be clearly observed on the mass spectrum after the photoreaction (see FIG. 27).

Example 14

[N-(2,4-dinitrophenyl)-L-leucyl]-L-glycine LEU-GLY

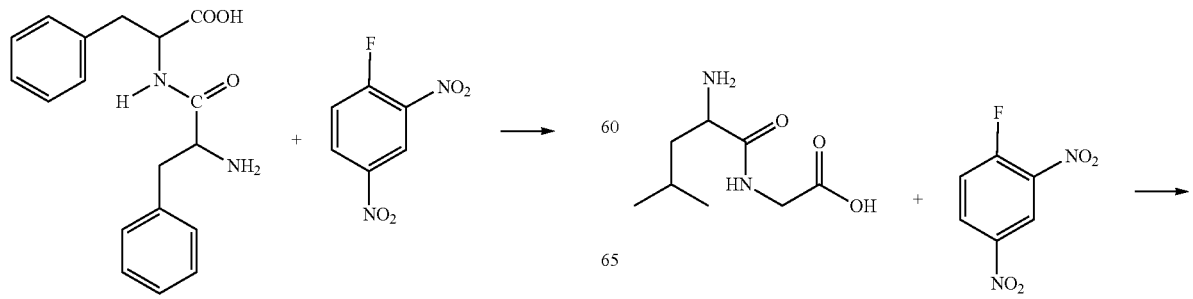

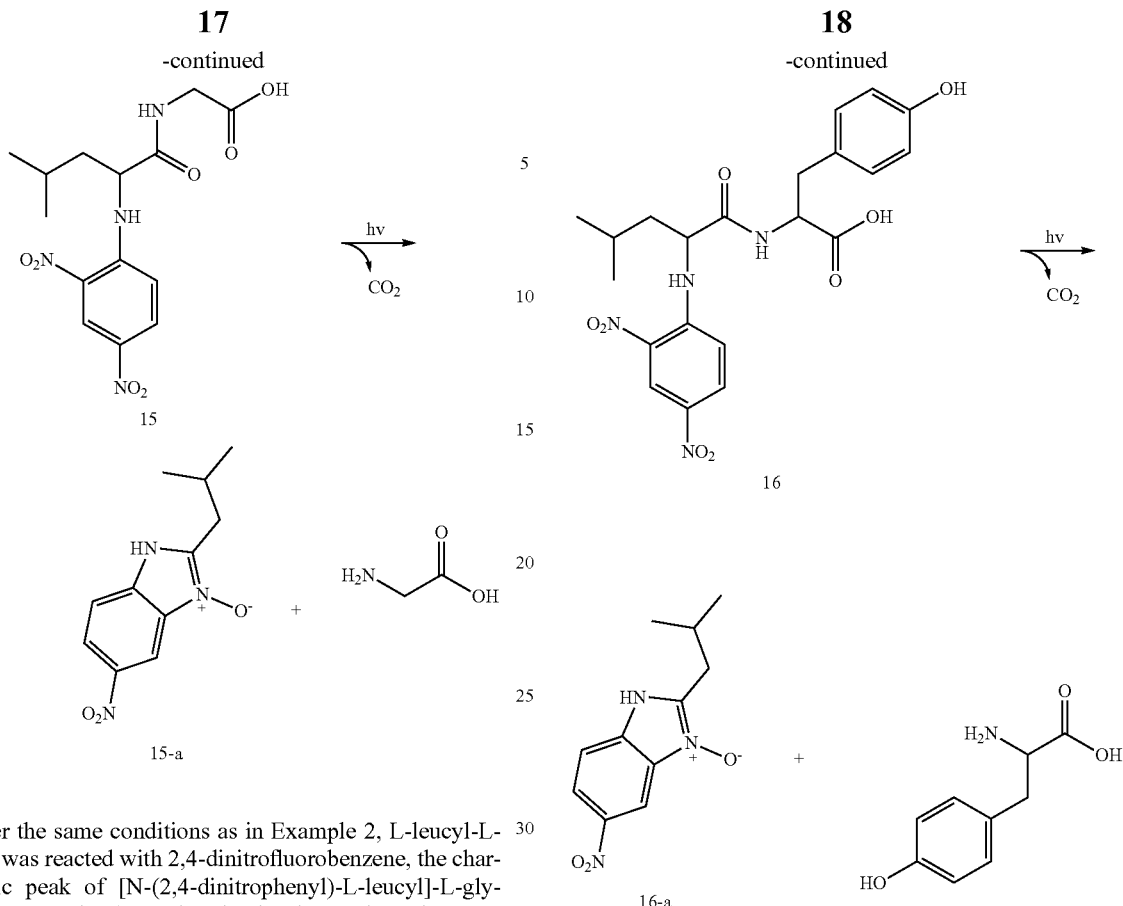

Figure 28:
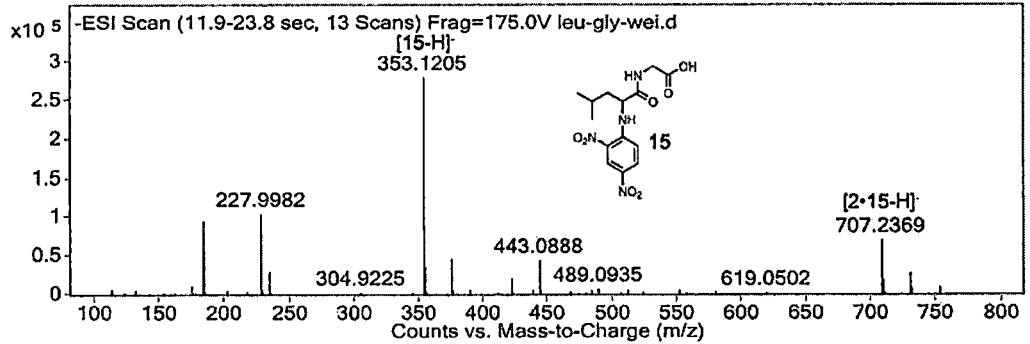
FIG. 28 and FIG. 29 are high-resolution mass spectra of compound 15 and after photoreaction.
Figure 29:
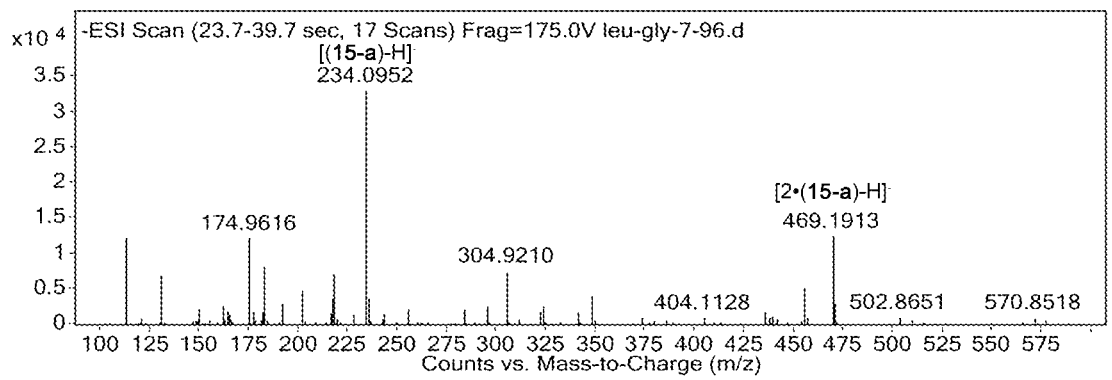

Under the same conditions as in Example 2, L-leucyl-L-glycine was reacted with 2,4-dinitrofluorobenzene, the characteristic peak of [N-(2,4-dinitrophenyl)-L-leucyl]-L-glycine (compound 15) can be clearly observed on the mass spectrum data after the reaction (see FIG. 28). Under the same conditions as in Example 2, [N-(2,4-dinitrophenyl)-L-leucyl]-L-glycine was subjected to a photocleavage reaction, the characteristic peak of 2-isobutyl-5-nitro-1H-benzo[d]imidazole-3-oxide (15-a) can be clearly observed on the mass spectrum data after the reaction (see FIG. 29).

Example 15

[N-(2,4-dinitrophenyl)-L-leucyl]-L-tyrosine LEU-tyr

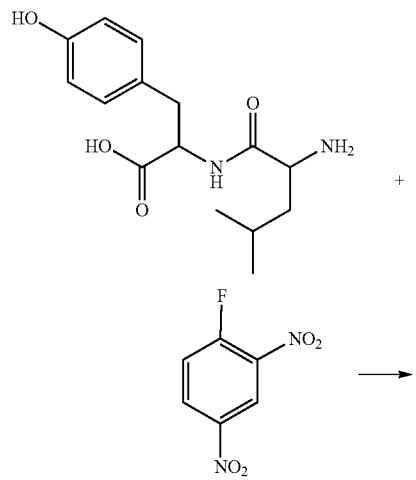

Figure 30:
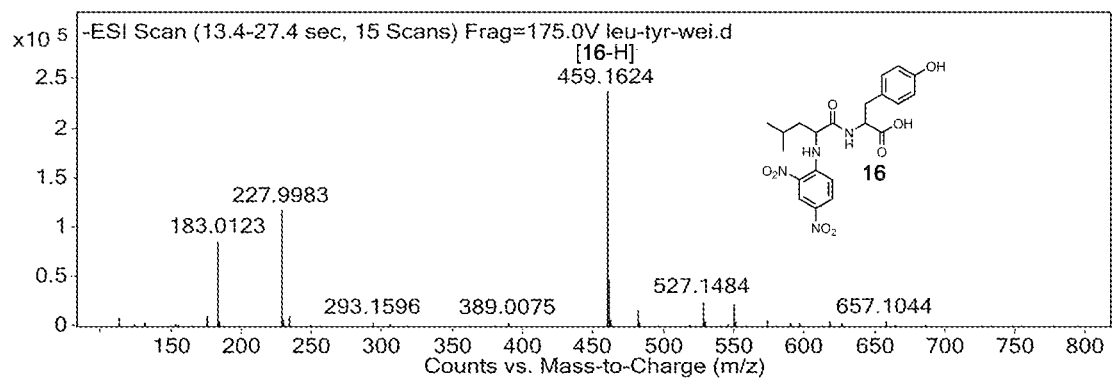
FIG. 30 and FIG. 31 are high-resolution mass spectra of compound 16 and after photoreaction.
Figure 31:
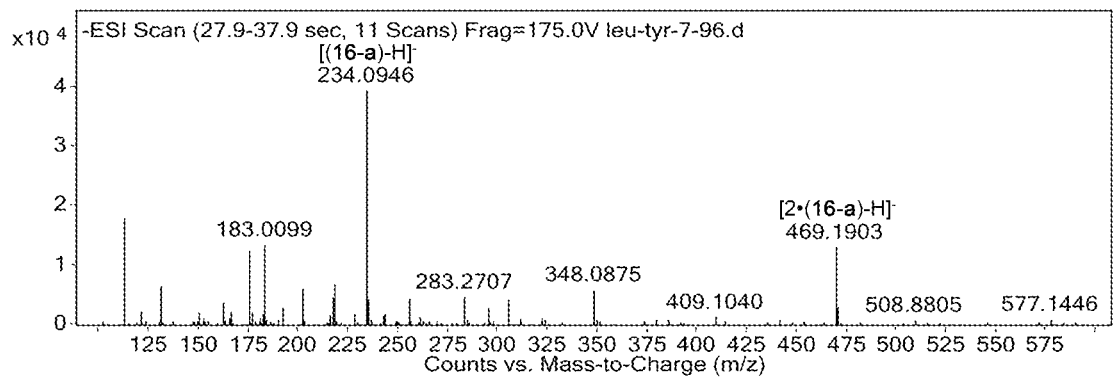

Under the same conditions as in Example 2, L-leucyl-L-tyrosine was reacted with 2,4-dinitrofluorobenzene, under the same conditions as in Example 2, L-leucyl-L-tyrosine was reacted with 2,4-dinitrofluorobenzene, the characteristic peak of [N-(2,4-dinitrophenyl)-L-leucyl]-L-tyrosine (compound 16) can be clearly observed on the mass spectrum data after the reaction (see FIG. 30). Under the same conditions as in Example 2, [N-(2,4-dinitrophenyl)-L-leucyl]-L-tyrosine was subjected to a photocleavage reaction, the characteristic peak of 2-isobutyl-5-nitro-1H-benzo[d]imidazole-3-oxide (16-a) can be clearly observed on the mass spectrum after the photoreaction (see FIG. 31).

Example 16

[N-(2,4-dinitrophenyl)-L-leucyl]-L-valine leu-val

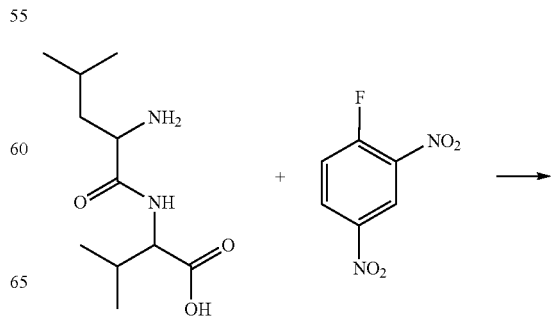

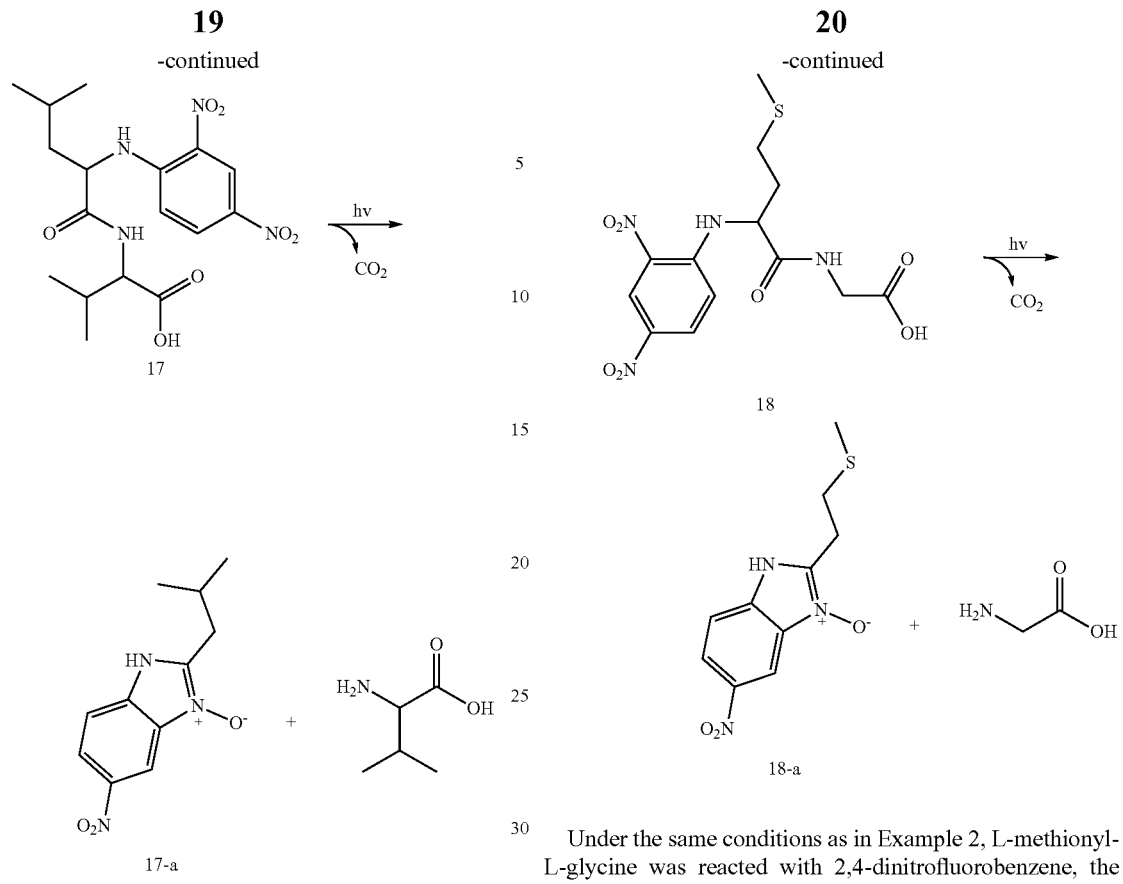

Figure 32:
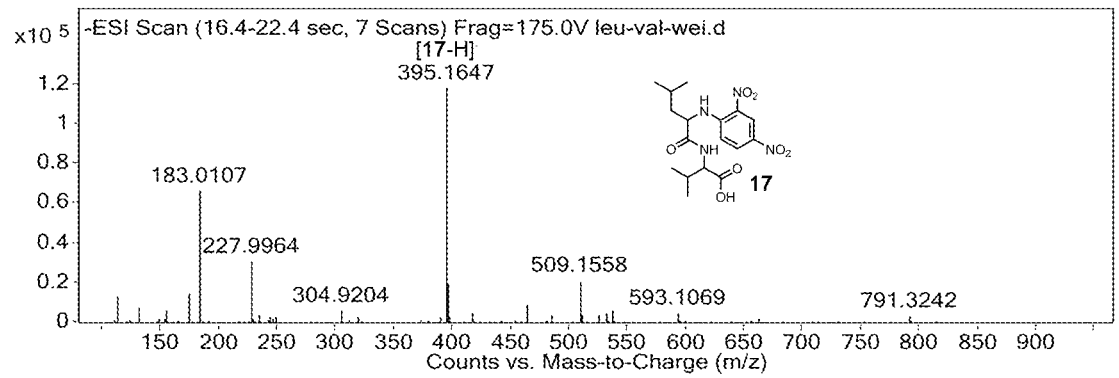
FIG. 32 and FIG. 33 are high-resolution mass spectra of compound 17 and after photoreaction.
Figure 33:
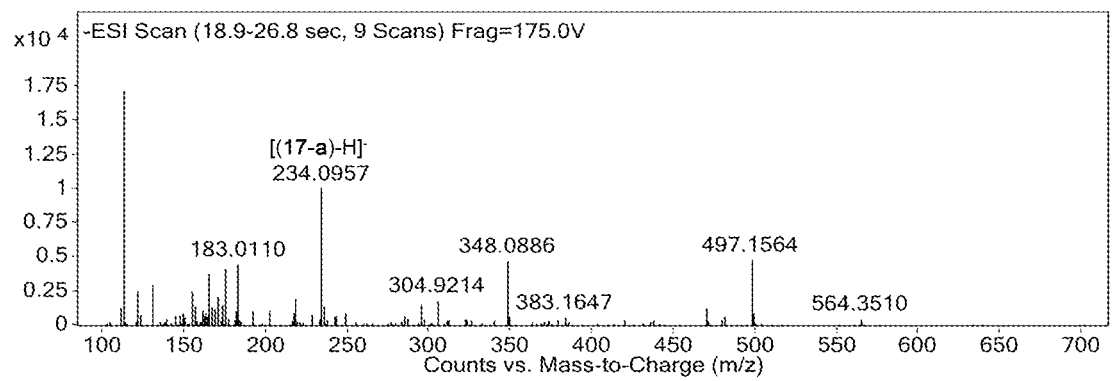

Under the same conditions as in Example 2, L-leucyl-L-valine was reacted with 2,4-dinitrofluorobenzene, the characteristic peak of [N-(2,4-dinitrophenyl)-L-leucyl]-L-valine (compound 17) can be clearly observed on the mass spectrum data after the reaction (see FIG. 32). Under the same conditions as in Example 2, [N-(2,4-dinitrophenyl)-L-leucyl]-L-valine was subjected to a photocleavage reaction, the characteristic peak of 2-isobutyl-5-nitro-1H-benzo[d]imidazole-3-oxide (17-a) can be clearly observed on the mass spectrum after the photoreaction (see FIG. 33).

Example 17

[N-(2,4-dinitrophenyl)-L-methionyl]-L-glycine
MET-GLY

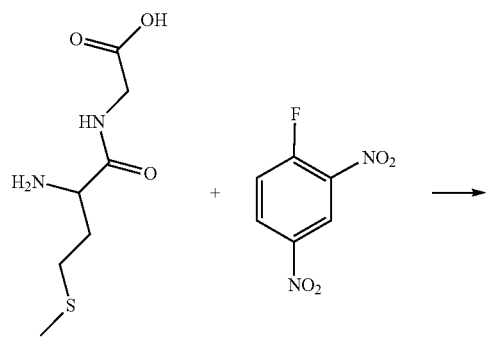

Figure 34:
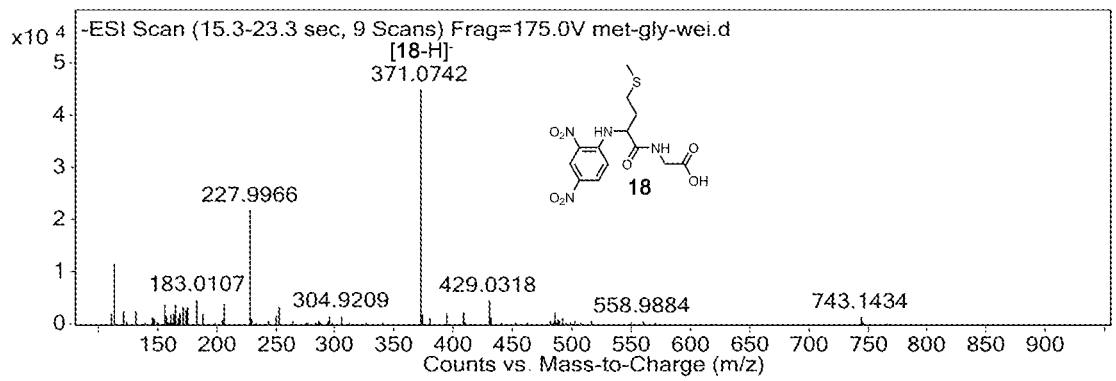
FIG. 34 and FIG. 35 are high-resolution mass spectra of compound 18 and after photoreaction.
Figure 35:
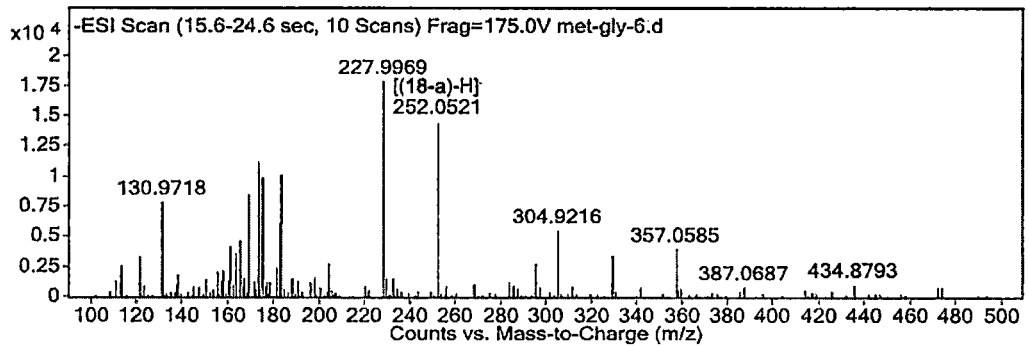

Under the same conditions as in Example 2, L-methionyl-L-glycine was reacted with 2,4-dinitrofluorobenzene, the characteristic peak of [N-(2,4-dinitrophenyl)-L-methionyl]-L-glycine (compound 18) can be clearly observed on the mass spectrum data after the reaction (see FIG. 34). Using deionized water with pH=6 instead of deionized water with pH=7, under the same conditions as in Example 2, [N-(2,4-dinitrophenyl)-L-methionyl]-L-glycine was subjected to a photocleavage reaction, the characteristic peak of 2-[2-(methylthio)ethyl]-5-nitro-1H-benzo[d]imidazole-3-oxide (18-a) can be clearly observed on the mass spectrum data after the reaction (see FIG. 35).

Example 18

[N-(2,4-dinitrophenyl)-L-phenylalanyl]-L-glycine
phe-GLY

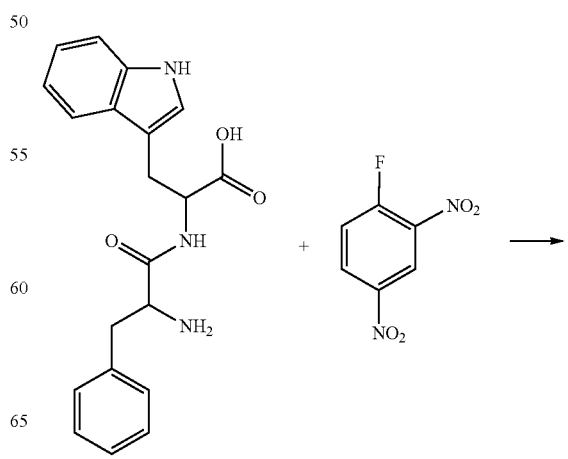

21

-continued

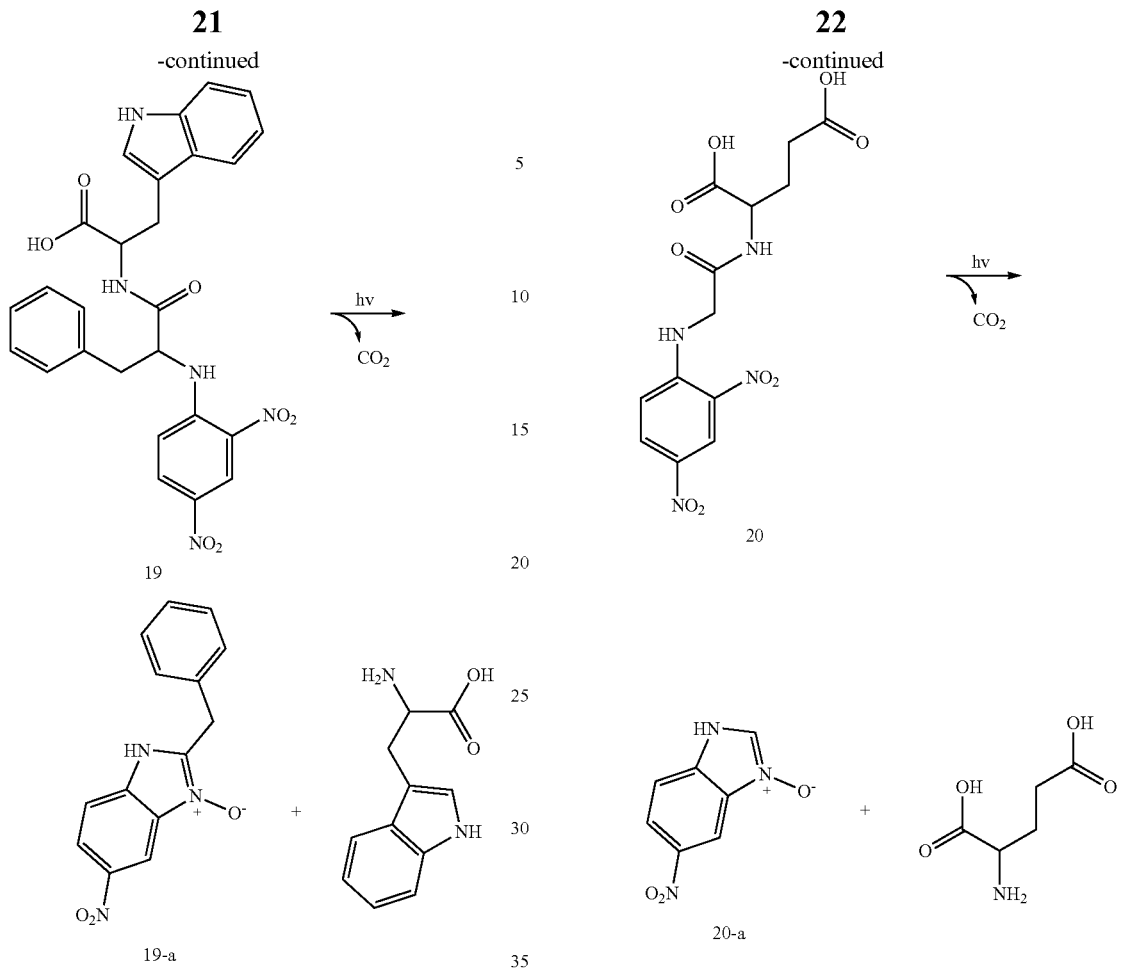

Figure 36:
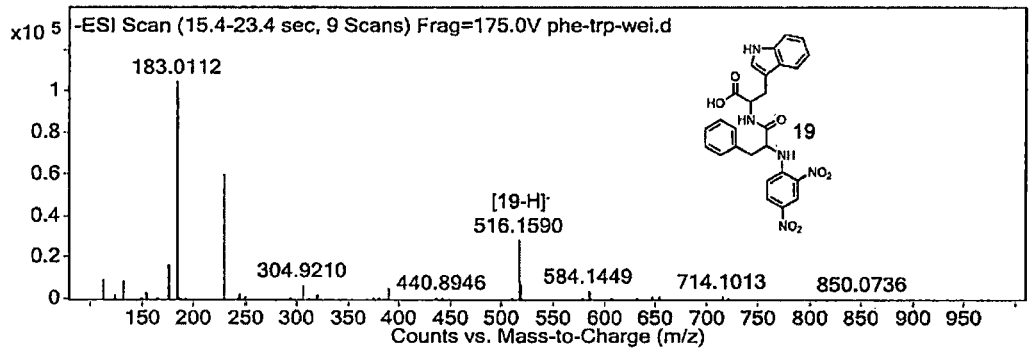
FIG. 36 and FIG. 37 are high-resolution mass spectra of compound 19 and after photoreaction.
Figure 37:
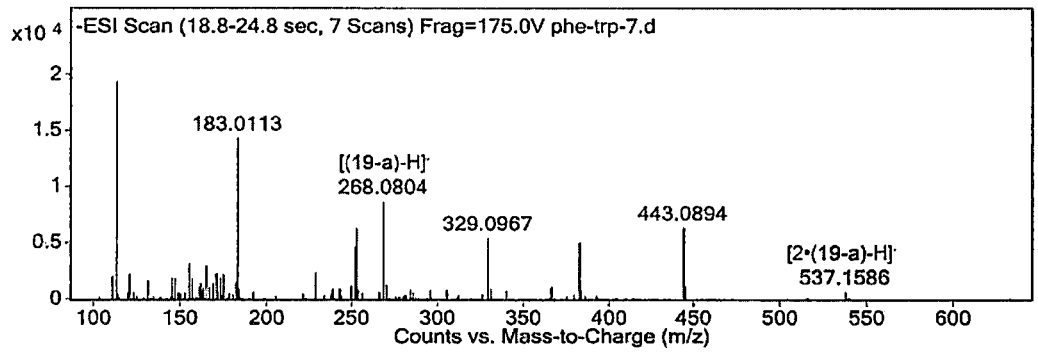

Under the same conditions as in Example 2, L-phenyl-alanyl-L-glycine was reacted with 2,4-dinitrofluorobenzene, the characteristic peak of [N-(2,4-dinitrophenyl)-L-phenyl-alanyl]-L-glycine (compound 19) can be clearly observed on the mass spectrum data after the reaction (see FIG. 36). Under the same conditions as in Example 2, [N-(2,4-dinitrophenyl)-L-phenylalanyl]-L-glycine was subjected to a photocleavage reaction, the characteristic peak of 2-benzyl-5-nitro-1H-benzo[d]imidazole-3-oxide (19-a) can be clearly observed on the mass spectrum after the photoreaction (see FIG. 37).

Figure 38:
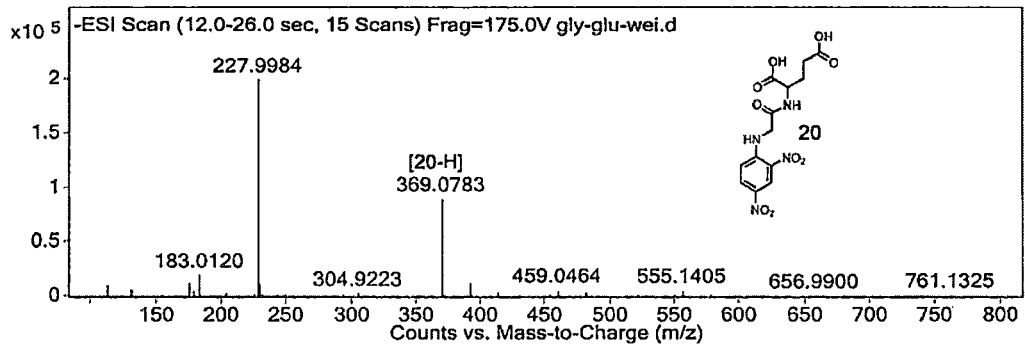
FIG. 38 and FIG. 39 are high-resolution mass spectra of compound 20 and after photoreaction.
Figure 39:
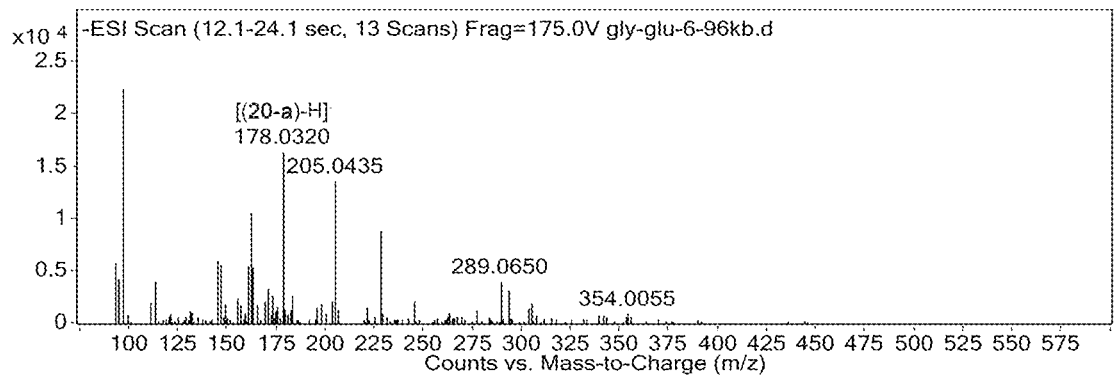

Under the same conditions as in Example 2, L-glycyl-L-glutamic acid was reacted with 2,4-dinitrofluorobenzene, the characteristic peak of [N-(2,4-dinitrophenyl)-L-glycyl]-L-glutamic acid (compound 20) can be clearly observed on the mass spectrum data after the reaction (see FIG. 38). Using deionized water of pH=6 instead of deionized water of pH=7, under the same conditions as in Example 2, [N-(2, 4-dinitrophenyl)-L-glycyl]-L-glutamic acid was subjected to a photocleavage reaction, and the characteristic peak of 5-nitro-1H-benzo[d]imidazole-3-oxide (20-a) can be clearly observed in the mass spectrum after the photoreaction (see FIG. 39).

Example 19

[N-(2,4-dinitrophenyl)-L-glycyl]-L-glutamic acid
GLY-glu

Example 20

[N-(2,4-dinitrophenyl)-L-valinyl]-L-alanine val-ala

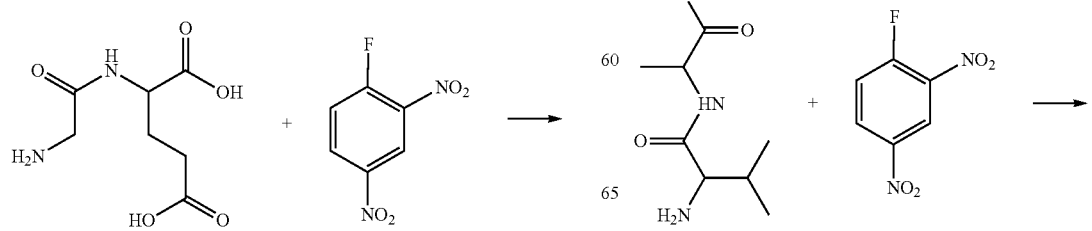

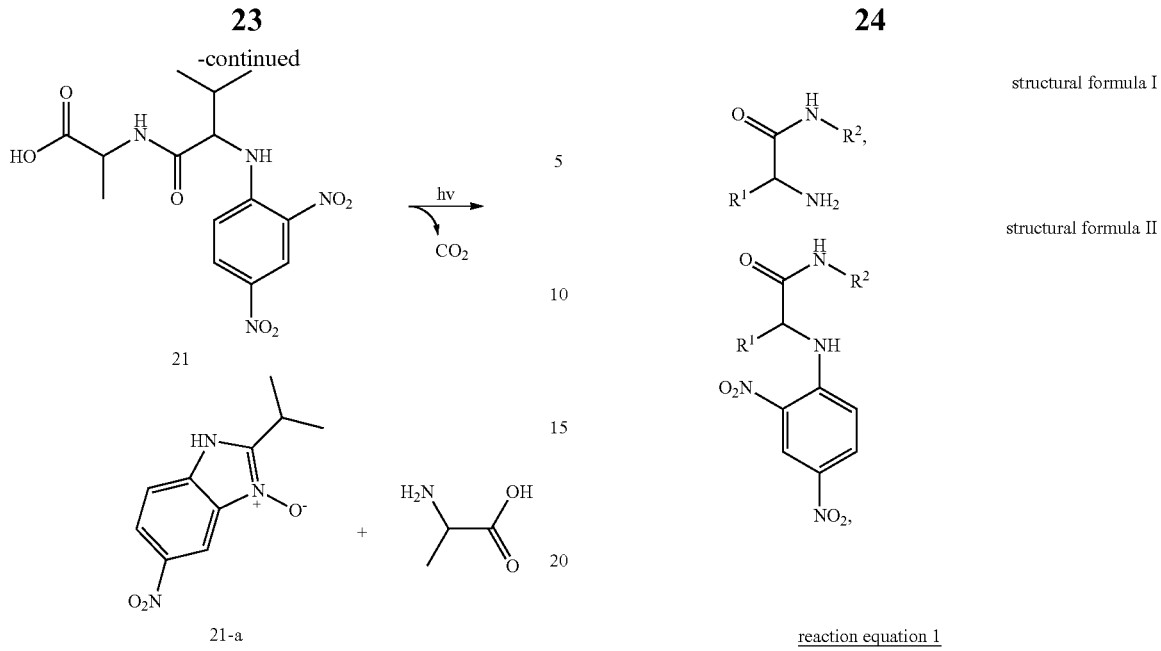

Figure 40:
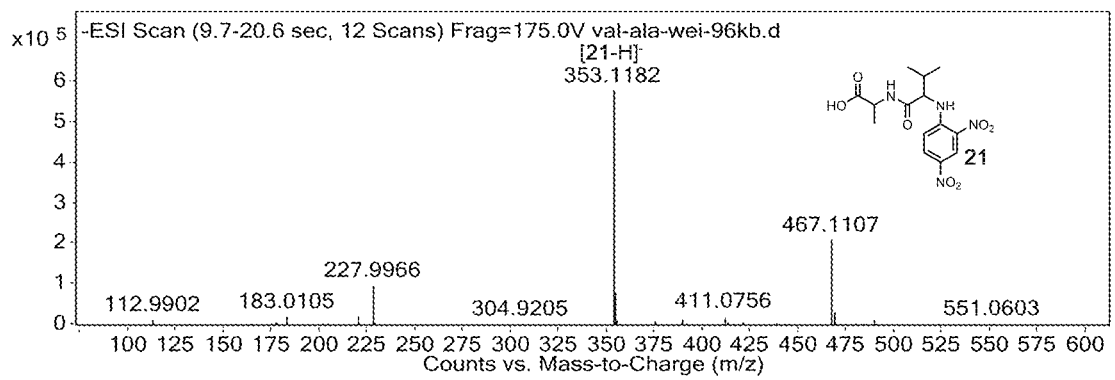
FIG. 40 and FIG. 41 are high-resolution mass spectra of compound 21 and after photoreaction.
Figure 41:
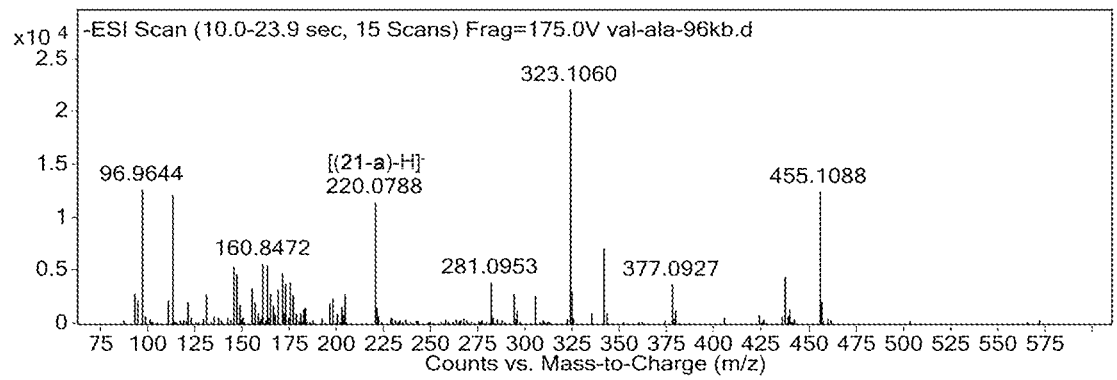

Under the same conditions as in Example 2, L-valinyl-L-alanine was reacted with 2,4-dinitrofluorobenzene, the characteristic peak of [N-(2,4-dinitrophenyl)-L-valinyl]-L-alanine (compound 21) can be clearly observed on the mass spectrum data after the reaction (see FIG. 40). Using deionized water with pH=6 instead of deionized water with pH=7, under the same conditions as in Example 2, [N-(2,4-dinitrophenyl)-L-valinyl]-L-alanine was subjected to a photocleavage reaction, the characteristic peak of 2-isopropyl-5-nitro-1H-benzo[d]imidazole-3-oxide (21-a) can be clearly observed on the mass spectrum after the photoreaction (see FIG. 41).

Example 21

[N-(2,4-dinitrophenyl)-L-prolyl]-glycine pro-gly

Figure 42:
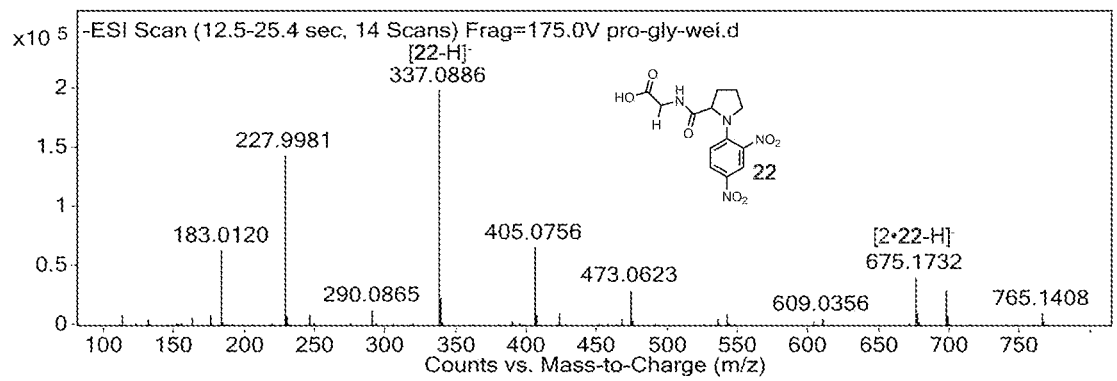
FIG. 42 and FIG. 43 are high-resolution mass spectra of compound 22 and after photoreaction.
Figure 43:
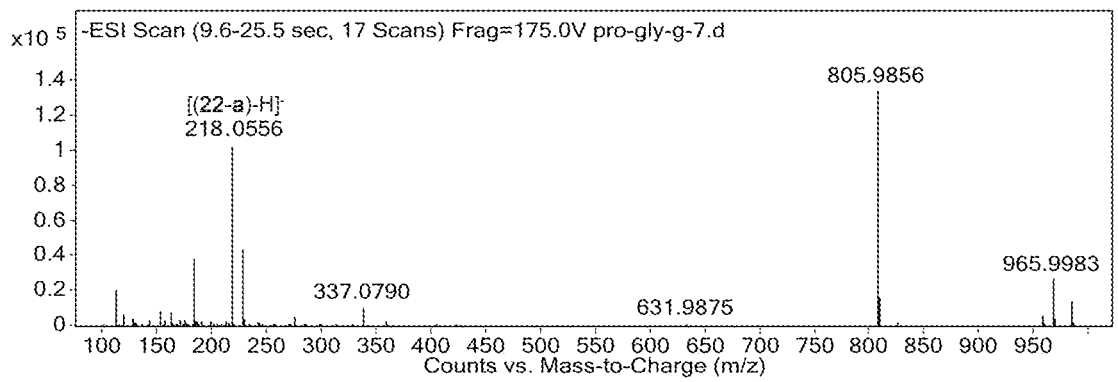

Under the same conditions as in Example 2, L-prolyl-L-glycine was reacted with 2,4-dinitrofluorobenzene, the characteristic peak of [N-(2,4-dinitrophenyl)-L-prolyl]-L-glycine (compound 22) can be clearly observed on the mass spectrum data after the reaction (see FIG. 42). Using deionized water with pH=6 instead of deionized water with pH=7, under the same conditions as in Example 2, [N-(2,4-dinitrophenyl)-L-prolyl]-L-glycine was subjected to a photocleavage reaction, the characteristic peak of 6-nitro-2,3-dihydro-1H-benzo[d]pyrrole[1,2-a]imidazole 4-oxide (22-a) can be clearly observed on the mass spectrum data after the reaction (see FIG. 43).

What is claimed is:

1. A method for photocleavage of an amide bond, comprising the steps of
   subjecting 2,4-dinitrofluorobenzene to a reaction with an amino group of a substance represented by structural formula I with an α-amino acid at an end to produce a compound 1 represented by structural formula II;
   under light irradiation, subjecting the compound 1 to a cleavage reaction of the amide bond according to reaction equation 1:

wherein $R^1$ is a side chain group of α-amino acid; $R^2$ aryl, aliphatic hydrocarbon group, or polypeptide group.

2. The method according to claim 1, further comprising the following steps: dissolving 2,4-dinitrofluorobenzene in an organic solvent to obtain a first solution, then dissolving the substance represented by structural formula I with an α-amino acid at the end and $NaHCO_3$ in water to obtain a second solution, mixing the first solution and the second solution in a reaction vessel, and stirring and refluxing a resulting mixture at 40-100° C. under darkness for 3-10 h.

3. The method according to claim 1, wherein a wavelength range for the light irradiation is 250-550 nm.

4. The method according to claim 1, wherein a light irradiation time is 0.1 second to 6 h.

5. The method according to claim 2, wherein the organic solvent is capable of dissolving the compound 1.

6. The method according to claim 5, wherein the organic solvent is one or a combination of dimethyl sulfoxide, alcohol, ketone, nitrile, ether, and amide.

7. The method according to claim 6, wherein the alcohol is methanol, ethanol, butanol, ethylene glycol, n-octanol or isopropanol; the ketone is acetone, methyl ethyl ketone, methyl isobutyl ketone or cyclohexanone; the nitrile is acetonitrile, propionitrile, isobutyronitrile, butyronitrile, malononitrile, benzonitrile, benzyl cyanide, succinonitrile or glutaronitrile; the ether is diethyl ether, tetrahydrofuran, dioxane, glycol dimethyl ether, 2-methyltetrahydrofuran or diphenyl ether; and the amide is N,N-dimethylformamide or N,N-dimethylacetamide.

\* \* \* \* \*